United States Patent
Kaditz et al.

(10) Patent No.: US 9,958,521 B2
(45) Date of Patent: May 1, 2018

(54) FIELD-INVARIANT QUANTITATIVE MAGNETIC-RESONANCE SIGNATURES

(71) Applicant: Tesla Health, Inc, Millbrae, CA (US)

(72) Inventors: Jeffrey Howard Kaditz, San Francisco, CA (US); Andrew Gettings Stevens, New York, NY (US)

(73) Assignee: Q Bio, Inc., San Francisco, CA (US)

( * ) Notice: Subject to any disclaimer, the term of this patent is extended or adjusted under 35 U.S.C. 154(b) by 79 days.

(21) Appl. No.: 15/089,571

(22) Filed: Apr. 3, 2016

(65) Prior Publication Data

US 2017/0011255 A1    Jan. 12, 2017

Related U.S. Application Data

(60) Provisional application No. 62/189,675, filed on Jul. 7, 2015, provisional application No. 62/233,291, filed
(Continued)

(51) Int. Cl.
*G06K 9/00* (2006.01)
*G01R 33/48* (2006.01)
(Continued)

(52) U.S. Cl.
CPC ............. *G01R 33/48* (2013.01); *G01N 24/08* (2013.01); *G01R 33/448* (2013.01);
(Continued)

(58) Field of Classification Search
None
See application file for complete search history.

(56) References Cited

U.S. PATENT DOCUMENTS

| 4,729,892 A | 3/1988 | Beall |
| 5,793,210 A | 8/1998 | Pla et al. |

(Continued)

FOREIGN PATENT DOCUMENTS

| WO | 2014205275 A1 | 12/2014 |
| WO | WO-2015183792 | 12/2015 |
| WO | WO-2016073985 | 5/2016 |

OTHER PUBLICATIONS

Hasenkam et al. "Prosthetic Heart Valve Evaluation by Magnetic Resonance Imaging." European Journal of Cardio-Thoracic Surgery 1999, pp. 300-305, 16, [Retrieved Aug. 25, 2016] <http://ejcts.oxfordjournals.org/content/16/3/300.full.pdf+html>.
(Continued)

*Primary Examiner* — Vikkram Bali
(74) *Attorney, Agent, or Firm* — Aurora Consulting LLC; Steven Stupp; Ashley Sloat

(57) ABSTRACT

A system that determines an invariant magnetic-resonance (MR) signature of a biological sample is disclosed. During operation, the system determines a magnetic-resonance (MR) model of voxels in a biological sample based on differences between MR signals associated with the voxels in multiple scans and simulated MR signals. The MR signals are measured or captured by an MR scanner in the system during multiple MR scans, and based on scanning instructions, and the simulated MR signals for the biological sample are generated using the MR model and the scanning instructions. Moreover, the system iteratively modifies the scanning instructions (including a magnetic-field strength and/or a pulse sequence) in the MR scans based on the differences until a convergence criterion is achieved. Then, the system stores, in memory, an identifier of the biological sample and a magnetic-field-strength-invariant MR signa-
(Continued)

ture of the biological sample that is associated with the MR model.

20 Claims, 13 Drawing Sheets

Related U.S. Application Data on Sep. 25, 2015, provisional application No. 62/233,288, filed on Sep. 25, 2015, provisional application No. 62/245,269, filed on Oct. 22, 2015, provisional application No. 62/250,501, filed on Nov. 3, 2015, provisional application No. 62/253,128, filed on Nov. 9, 2015, provisional application No. 62/255,363, filed on Nov. 13, 2015, provisional application No. 62/281,176, filed on Jan. 20, 2016.

(51) Int. Cl.
| | | |
|---|---|---|
| *G01N 24/08* | (2006.01) | |
| *G01R 33/44* | (2006.01) | |
| *G01R 33/465* | (2006.01) | |
| *G01R 33/563* | (2006.01) | |

(52) U.S. Cl.
CPC ........ *G01R 33/465* (2013.01); *G01R 33/4804* (2013.01); *G01R 33/56358* (2013.01)

(56) References Cited

U.S. PATENT DOCUMENTS

| 6,084,408 | A | 7/2000 | Chen |
| 6,148,272 | A | 11/2000 | Bergstrom et al. |
| 6,392,409 | B1 | 5/2002 | Chen |
| 7,924,002 | B2 | 4/2011 | Lu |
| 7,940,927 | B2 | 5/2011 | Futa et al. |
| 7,974,942 | B2 | 7/2011 | Pomroy |
| 8,432,165 | B2 | 4/2013 | Weiger Senften |
| 8,502,532 | B2 | 8/2013 | Assmann |
| 8,686,727 | B2 | 4/2014 | Reddy et al. |
| 8,723,518 | B2 | 5/2014 | Seiberlech et al. |
| 8,736,265 | B2 | 5/2014 | Boemert et al. |
| 9,513,359 | B2 | 12/2016 | Koch |
| 9,514,169 | B2 | 12/2016 | Mattsson |
| 2002/0155587 | A1 | 10/2002 | Opalsky |
| 2002/0177771 | A1 | 11/2002 | Guttman et al. |
| 2003/0210043 | A1 | 11/2003 | Freedman |
| 2005/0137476 | A1 | 6/2005 | Welland |
| 2005/0181466 | A1 | 8/2005 | Dambinova |
| 2008/0065665 | A1 | 3/2008 | Pomroy |
| 2008/0081375 | A1 | 4/2008 | Tesiram et al. |
| 2008/0082834 | A1 | 4/2008 | Mattsson |
| 2009/0315561 | A1 | 12/2009 | Assmann |
| 2010/0131518 | A1 | 5/2010 | Eltet |
| 2010/0142823 | A1 | 6/2010 | Wang et al. |
| 2010/0177188 | A1 | 7/2010 | Kishima |
| 2010/0189328 | A1 | 7/2010 | Boemert et al. |
| 2010/0244827 | A1 | 9/2010 | Hennel |
| 2010/0306854 | A1 | 12/2010 | Neergaard |
| 2011/0044524 | A1* | 2/2011 | Wang .................... G01R 33/54 382/131 |
| 2011/0095759 | A1 | 4/2011 | Bhattacharya et al. |
| 2011/0166484 | A1 | 7/2011 | Virta |
| 2012/0124161 | A1 | 5/2012 | Tudwell et al. |
| 2013/0275718 | A1 | 10/2013 | Ueda |
| 2013/0294669 | A1* | 11/2013 | El-Baz .................... G06T 7/42 382/131 |
| 2013/0338930 | A1* | 12/2013 | Senegas ............... G01R 33/543 702/19 |
| 2014/0062475 | A1 | 3/2014 | Koch |
| 2014/0336998 | A1 | 11/2014 | Cecchi |
| 2015/0003706 | A1 | 1/2015 | Eftestol et al. |
| 2015/0032421 | A1 | 1/2015 | Dean et al. |
| 2015/0040225 | A1 | 2/2015 | Coates et al. |
| 2015/0089574 | A1 | 3/2015 | Mattsson |
| 2016/0007968 | A1 | 1/2016 | Sinkus |
| 2016/0127123 | A1 | 5/2016 | Johnson |
| 2017/0011514 | A1 | 1/2017 | Westerhoff |
| 2017/0038452 | A1 | 2/2017 | Trzasko |

OTHER PUBLICATIONS

Nestares, et al. "Robust Multiresolution Alignment of MRI Brain Volumes." Magnetic Resonance in Medicine 2000, pp. 705-715, [Retrieved Aug. 27, 2016] <http://web.mit.edu/ImagingPubs/Coregistration/nestares_heeger_coreg.pdf>.

International Search Report and Written Opinion dated Nov. 28, 2016 re PCT/US16/51204.

International Search Report and Written Opinion dated Sep. 19, 2016 re PCT/US16/040578.

International Search Report and Written Opinion dated Sep. 19, 2016 re PCT/US16/040215.

"International Application Serial No. PCT/US2017/022842, Written Opinion dated May 23, 2017, PCT report opinion dated May 23, 2017", 4 pgs.

"International Application Serial No. PCT/US2017/022842, International Search Report dated May 23, 2017, PCT search report dated May 23, 2017", 2 pgs.

International Application Serial No. PCT/US2017/022911, International Search Report dated Jul. 19, 2017, 4 pgs.

International Application Serial No. PCT/US2017/022911, Written Opinion dated Jul. 19, 2017, 10 pgs.

International Application Serial No. PCT/US2017/035071, International Search Report dated Aug. 22, 2017, 2 pgs.

International Application Serial No. PCT/US2017/035071, Written Opinion dated Aug. 22, 2017, 7 pgs.

International Application Serial No. PCT/US2017/035073, International Search Report dated Aug. 11, 2017, 2 pgs.

G. Schultz, "Magnetic Resonance Imaging with Nonlinear Gradient Fields: Signal Encoding and Image Reconstruction", Springer Verlag, New York, 2013).

Siemens, "Magnetic Resonance Imaging", (Dec. 2012) [retrieved on Jun. 27, 2017, https://w5.siemens.com/web/ua/ru/medecine/detection_diagnosis/magnetic_resonans/035-15-MRI-scaners/Documents/mri-magnetom-family_brochure-00289718.pdf].

International Application Serial No. PCT/US2017/035073, Written Opinion dated Aug. 11, 2017, 6 pgs.

Gualda et al., "SPIM-fluid: open source light-sheet based platform for high-throughput imaging", Biomed Opt Express (Nov. 1, 2015) vol. 6, No. 11.

* cited by examiner

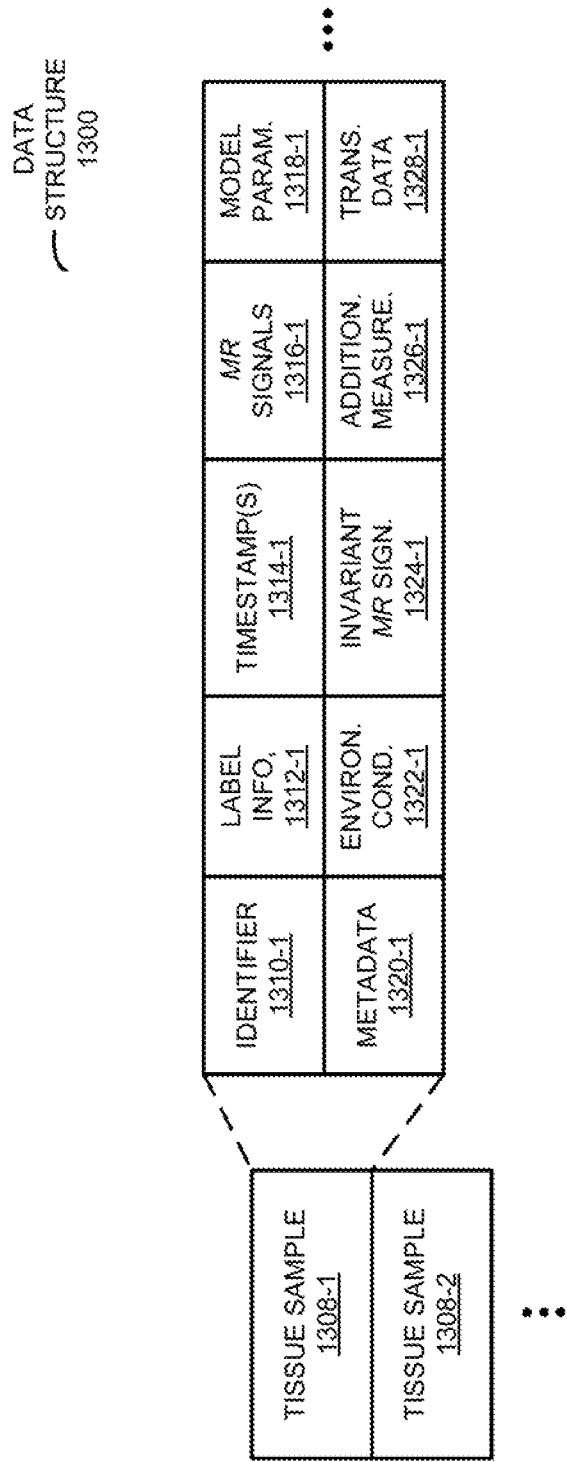

FIELD-INVARIANT QUANTITATIVE MAGNETIC-RESONANCE SIGNATURES

CROSS-REFERENCE TO RELATED APPLICATION

The is application claims priority under 35 U.S.C. § 119(e) to: U.S. Provisional Application Ser. No. 62/189,675, entitled "Systems and Method for Indexed Medical Imaging of a Subject Over Time," by Jeffrey H. Kaditz and Andrew G. Stevens, filed on Jul. 7, 2015; U.S. Provisional Application Ser. No. 62/233,291, entitled "Systems and Method for Indexed Medical Imaging of a Subject Over Time," by Jeffrey H. Kaditz and Andrew G. Stevens, filed on Sep. 25, 2015; U.S. Provisional Application Ser. No. 62/233,288, entitled "Systems and Method for Indexed Medical and/or Fingerprinting Tissue," by Jeffrey H. Kaditz and Andrew G. Stevens, filed on Sep. 25, 2015; U.S. Provisional Application Ser. No. 62/245,269, entitled "System and Method for Auto Segmentation and Generalized MRF with Minimized Parametric Mapping Error Using A Priori Knowledge," by Jeffrey H. Kaditz, filed on Oct. 22, 2015; U.S. Provisional Application Ser. No. 62/250,501, entitled "System and Method for Auto Segmentation and Generalized MRF with Minimized Parametric Mapping Error Using A Priori Knowledge," by Jeffrey H. Kaditz, filed on Nov. 3, 2015; U.S. Provisional Application Ser. No. 62/253,128, entitled "System and Method for Auto Segmentation and Generalized MRF with Minimized Parametric Mapping Error Using A Priori Knowledge," by Jeffrey H. Kaditz, filed on Nov. 9, 2015; U.S. Provisional Application Ser. No. 62/255,363, entitled "System and Method for Auto Segmentation and Generalized MRF with Minimized Parametric Mapping Error Using A Priori Knowledge," by Jeffrey H. Kaditz, filed on Nov. 13, 2015; and U.S. Provisional Application Ser. No. 62/281,176, entitled "System and Method for Auto Segmentation and Generalized MRF with Minimized Parametric Mapping Error Using A Priori Knowledge," by Jeffrey H. Kaditz, filed on Jan. 20, 2016, the contents of each of which are herein incorporated by reference.

BACKGROUND

Field

The described embodiments relate generally magnetic resonance (MR), more specifically to characterizing tissue based on one or more medical resonance techniques, such as magnetic resonance imaging (MRI), magnetic resonance spectral imaging (MRSI) and/or magnetic resonance fingerprinting (MRF).

Related Art

Magnetic resonance or MR (which is often referred to as 'nuclear magnetic resonance' or NMR) is a physical phenomenon in which nuclei in a magnetic field absorb and re-emit electromagnetic radiation. For example, magnetic nuclear spins may be partially aligned (or polarized) in an applied external magnetic field. These nuclear spins may precess or rotate around the direction of the external magnetic field at an angular frequency (which is sometimes referred to as the 'Larmor frequency') given by the product of a gyromagnetic ratio of a type of nuclei and the magnitude or strength of the external magnetic field. By applying a perturbation to the polarized nuclear spins, such as one or more radio-frequency (RF) pulses (and, more generally, electromagnetic pulses) having pulse widths corresponding to the angular frequency and at a right-angle or perpendicular to the direction of the external magnetic field, the polarization of the nuclear spins can be transiently changed. The resulting dynamic response of the nuclear spins (such as the time-varying total magnetization) can provide a wealth of information about the physical and material properties of a sample.

In medicine, MR has been widely used to non-invasively determine anatomical structure and/or the chemical composition of different types of tissue. For example, in magnetic resonance imaging (MRI), the dependence of the angular frequency of precession of nuclear spins (such as protons or the isotope $^1$H) on the magnitude of the external magnetic field is used to determine images of anatomical structure. In particular, by applying a non-uniform or spatially varying magnetic field to a patient, the resulting variation in the angular frequency of precession of $^1$H spins is typically used to spatially localize the measured dynamic response of the $^1$H spins to voxels, which can be used to generate images of the internal anatomy of the patient. Alternatively, in magnetic resonance spectral imaging (MRSI) the measured dynamic response of other nuclei in addition to $^1$H are often used to generate images of the chemical composition or the morphology of different types of tissue and the internal anatomy of the patient.

Typically, existing MR techniques such as MRI or MRSI are used to measure a limited set of physical or material properties. Moreover, these MR techniques usually provide qualitative or 'weighted' measurement of these properties. In particular, the MR signal intensity is rarely quantitative by itself. Instead, analysis of MR signals often involves relative comparisons of spectral peaks, spatial locations or different points in time.

Recently, researchers have used MR to measure multiple parameters simultaneously and to provide quantitative measurements of sample properties. In particular, instead of using repeated, serial acquisition of data to characterize individual parameters that are of interest, in magnetic resonance fingerprinting (MRF) signals from different materials or tissues are usually acquired using a pseudorandom pulse sequence to determine a unique signal or 'fingerprint' (e.g., a time-dependent magnetization or MR trajectory) that is a function of multiple material properties under investigation. In principle, using pattern-recognition techniques the quantitative multi-parameter fingerprint can be matched to predefined states (such as the presence of a particular disease) and can improve measurement accuracy.

Because the spatial resolution of MR techniques usually depends on the magnitude of magnetic field gradient, there are ongoing efforts to increase the magnetic field strength, e.g., using superconductors. However, the use of large magnetic-field strengths usually increases the size and cost of an MR scanner.

In addition, because of measurement variation from scanner to scanner, and even among repeated measurements performed by the same scanner, it has proven difficult to perform reliable or reproducible quantitative MR measurements. Consequently, in spite of the wide-spread use of MR in medicine, the true potential of this powerful measurement technique still has not been achieved, which can be frustrating to healthcare providers and can adversely impact patient outcomes.

SUMMARY

Some embodiments relate to a system that determines an invariant MR signature. This system determines a magnetic-resonance (MR) model of voxels at three-dimensional (3D) positions in a biological sample based on differences of MR signals associated with the voxels and simulated MR signals. In particular, the MR signals are captured during multiple MR scans of one or more types of nuclei in the biological sample performed by an MR scanner based on scanning instructions (such as while performing magnetic-resonance fingerprinting or MRF of the biological sample), and the simulated MR signals for the biological sample are generated using the MR model and the scanning instructions. Note that an instance of the scanning instructions includes or specifies at least a magnetic-field strength and a pulse sequence that are applied to the biological sample, and the system iteratively modifies the scanning instructions (including the magnetic-field strength and/or the pulse sequence) in the MR scans based on the differences until a convergence criterion is achieved. Then, the system stores, in memory, an identifier of the biological sample and the invariant MR signature that is associated with the MR model and that describes a dynamic MR response of the biological sample at an arbitrary magnetic-field strength.

Note that the identifier may uniquely identify the biological sample. Moreover, the system may generate the identifier. Alternatively, the system may receive the identifier. For example, the system may include a sample-information reader that provides or measures information that specifies the identifier.

Furthermore, the system may include a measurement device that measures a physical property of the biological sample. In particular, the measurement device may provide physical property information that specifies the measured physical property. The system may store the physical property information in the memory with the identifier and the invariant MR signature. For example, the physical property may include: a weight of the biological sample; one or more dimensions of the biological sample; an impedance of the biological sample; and/or an image of the biological sample. Note that the measurement device may include: an imaging sensor; a scale; an impedance analyzer; a laser imaging system; and/or a microscope.

Additionally, the MR scanner may include a bore-type MR scanner having a bore diameter between 1 and 10 cm. The bore-type MR scanner may be enclosed in a chamber, defined by a surface, that, during operation of the system, is filled with an inert gas or that has a pressure less than atmospheric pressure. Alternatively, the biological sample may be enclosed in a vessel that is filled with an inert gas or that has a pressure less than atmospheric pressure.

In some embodiments, the system encrypts the determined invariant MR signature prior before storing it in the memory.

Moreover, the biological sample may be formalin fixed-paraffin embedded, and the system may transform the invariant MR signature into an estimated invariant MR signature of an in-vivo sample based on the MR model. Alternatively, the biological sample may include an in-vivo sample.

Furthermore, the system may: compare the determined invariant MR signature to one or more predetermined invariant MR signatures (or may compare an MR fingerprint calculated from or based on the determined invariant MR signature with one or more predetermined MR fingerprints); determine a classification of the biological sample based on the comparisons; and store the determined classification in the memory with the identifier and the invariant MR signature.

Additionally, the system may: perform an additional MR measurement on the biological sample; and may store a result of the additional MR measurement in the memory with the identifier and the invariant MR signature. For example, the additional MR measurement may include: magnetic-resonance thermometry (MRT), magnetic-resonance spectroscopy (MRS), magnetic-resonance imaging (MRI), magnetic-field relaxometry, and/or magnetic-resonance elastography (MRE).

Another embodiment provides a computer-program product for use with the system. This computer-program product includes instructions for at least some of the aforementioned operations performed by the system.

Another embodiment provides a method for determining an invariant MR signature of the biological sample using the MR scanner. This method includes at least some of the aforementioned operations performed by the system.

Another embodiment provides a second system (which may be different than or the same as the system) that collects additional information during an MR scan, including: MR signals from a biological sample, the applied non-ideal pulse sequences, and measured noise. This information may facilitate accurate simulations of the MR scan and the biological sample, e.g., by training an MR model.

Another embodiment provides a computer-program product for use with the second system. This computer-program product includes instructions for at least some of the aforementioned operations performed by the second system.

Another embodiment provides a method for performing an MR scan using the second system. This method includes at least some of the aforementioned operations performed by the second system.

This Summary is provided merely for purposes of illustrating some exemplary embodiments, so as to provide a basic understanding of some aspects of the subject matter described herein. Accordingly, it will be appreciated that the above-described features are simply examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE FIGURES

FIG. 5 4 is a drawing illustrating a simulated MR signal and the set of MR signals in FIG. 4 as a function of time in accordance with an embodiment of the present disclosure.

FIG. 13 is a drawing illustrating a data structure that is used by the electronic device of FIG. 7 in accordance with an embodiment of the present disclosure.

Note that like reference numerals refer to corresponding parts throughout the drawings. Moreover, multiple instances of the same part are designated by a common prefix separated from an instance number by a dash.

DETAILED DESCRIPTION

Figure 1:
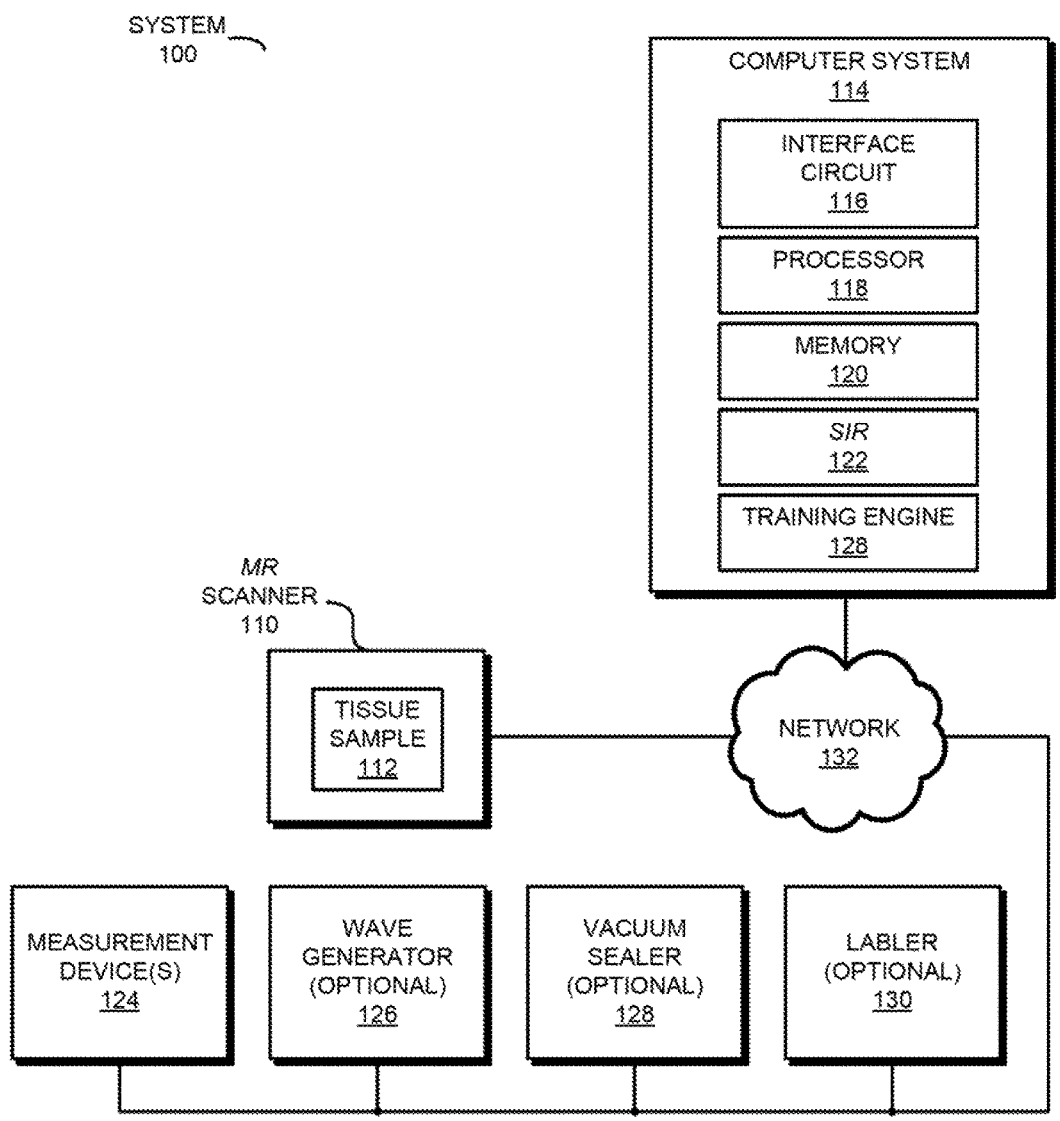
FIG. 1 is a block diagram illustrating a system with a magnetic-resonance (MR) scanner that determines an invariant MR signature of a biological sample in accordance with an embodiment of the present disclosure.

A system that determines an invariant magnetic-resonance (MR) signature of a biological sample is disclosed. During operation, the system determines a magnetic-resonance (MR) model of voxels in a biological sample based on differences between MR signals associated with the voxels in multiple scans and simulated MR signals. The MR signals are measured or captured by an MR scanner in the system during multiple MR scans (such as while performing magnetic-resonance fingerprinting or MRF), and based on scanning instructions, and the simulated MR signals for the biological sample are generated using the MR model and the scanning instructions. Moreover, the system iteratively modifies the scanning instructions (including at least a magnetic-field strength, a pulse sequence, an MR technique, a region of interest in the biological sample, a voxel size and/or a type of nuclei) in the MR scans based on the differences until a convergence criterion is achieved. Then, the system stores, in memory, an identifier of the biological sample and the invariant MR signature that is associated with the MR model (such as parameters in the MR model) and that describes a dynamic MR response of the biological sample at an arbitrary magnetic-field strength.

By determining the invariant MR signature, this characterization technique may allow quantitatively accurate MR scans to be performed on the biological sample in the same MR scanner or a different MR scanner. This quantitative capability may improve the accuracy and/or decrease the scan time for the MR scans. Consequently, the characterization technique may significantly reduce the cost of the MR scans and may reduce patient frustration (and, thus, may increase patient satisfaction) with MR scans.

Furthermore, the invariant MR signature may facilitate longitudinal analysis of changes in the biological sample and/or aggregate analysis of multiple MR fingerprints (which were acquired in different MR scanners). Therefore, the characterization technique may facilitate improved analysis of MR fingerprints and improved patient outcomes.

Additionally, the invariant MR signature may be used to quantitatively characterize an MR scanner (such as magnetic-field variations or spatial inhomogeneity, detector noise, etc.) and can be used to predict the MR signals during MR scans in a particular MR scanner. These capabilities may allow the use of an MR scanner with smaller and/or less homogeneous magnetic fields, which may reduce the size and the cost of the MR scanner.

In the discussion that follows, the characterization technique may be used in conjunction with a variety of MR techniques, including: magnetic resonance imaging (MRI), magnetic resonance spectroscopy (MRS), magnetic resonance spectral imaging (MRSI), MRF, magnetic-resonance elastography (MRE), magnetic-resonance thermometry (MRT), magnetic-field relaxometry, and/or another MR technique (such as functional MRI, metabolic imaging, molecular imaging, blood-flow imaging, etc.).

In particular, 'MRI' should be understood to include generating images (such as 2D slices) or maps of internal structure in a sample (such as anatomical structure in a biological sample, e.g., a tissue sample or a patient) based on the dynamic response of a type of nuclear spin (such protons or the isotope $^1$H) in the presence of a magnetic field, such as a non-uniform or spatially varying external magnetic field (e.g., an external magnetic field with a well-defined spatial gradient). Moreover, 'magnetic resonance spectroscopy' or 'MR spectroscopy' should be understood to include determining chemical composition or morphology of a sample (such as a biological sample) based on the dynamic response of multiple types of nuclear spins (other than or in addition to $^1$H) in the presence of a magnetic field, such as a uniform external magnetic field. Furthermore, 'MRSI' should be understood to include generating images or maps of internal structure and/or chemical composition or morphology in a sample using MR spectroscopy in the presence of a magnetic field, such as a non-uniform or spatially varying external magnetic field.

Additionally, 'MRF' should be understood to include quantitative measurements of the properties of a sample by acquiring signals representing a dynamic or time-dependent magnetization or MR trajectory from different materials in a sample using a pseudorandom pulse sequence. The resulting unique 'fingerprint' of the sample is, in general, a function of multiple material properties under investigation. For example, MRF can provide high-quality quantitative maps of: the spin-lattice relaxation time $T_1$ (which is the time constant associated with the loss of signal intensity as components of the nuclear-spin magnetization vector relax to be parallel with the direction of an external magnetic field), the spin-spin relaxation time $T_2$ (which is the time constant associated with broadening of the signal during relaxation of components of the nuclear-spin magnetization vector perpendicular to the direction of the external magnetic field), proton density (and, more generally, the densities of one or more type of nuclei) and diffusion (such as components in a diffusion tensor).

Note that 'magnetic-field relaxometry' (such as $B_0$ relaxometry with the addition of a magnetic-field sweep) may involve acquiring MR images at different magnetic-field strengths. These measurements may be performed on the fly or dynamically (as opposed to performing measurements at a particular magnetic-field strength and subsequently cycling back to a nominal magnetic-field strength during readout, i.e., a quasi-static magnetic-field strength). For example, the measurements may be performed using untuned radio-frequency (RF) coils or a magnetometer so that measurements at the different magnetic-field strengths can be performed in significantly less time.

Moreover, in the discussion that follows 'MRE' should be understood to include measuring the stiffness of a sample using MRI by sending mechanical waves (such as sheer waves) through a sample, acquiring images of the propagation of the shear waves, and processing the images of the shear waves to produce a quantitative mapping of the sample stiffness (which are sometimes referred to as 'elastograms').

Furthermore, 'MRT' should be understood to include measuring maps of temperature change in a sample using MRI.

In the discussion that follows, note that a biological sample may include a tissue sample from an animal or a person (i.e., a portion of the animal or the person). For example, the tissue sample may have been previously removed from the animal or the person. In some embodiments, the tissue sample is a pathology sample, such as a biopsy sample. Thus, the tissue sample may be formalin fixed-paraffin embedded. However, in other embodiments a biological sample may be in the animal or the person (i.e., an in-vivo sample) and/or the characterization technique involves whole-body scans. Furthermore, the characterization technique may also be applied to inanimate (i.e., non-biological) samples of a wide variety of different materials. Moreover, while the characterization technique may be used with a wide variety of MR techniques, in the discussion that follows MRF is used as an illustrative example.

We now describe embodiments of a system. This system may determine an MR fingerprint that is magnetic field invariant (which are sometimes referred to as a 'magnetic-field-invariant MR signature' or an 'invariant MR signature') of a tissue sample using a variation on MRF (which is sometimes referred to as 'quantitative MRF' or QMR-X). The system may also measure additional information such as diagnostic information or metadata associated with the tissue sample, including: weight, size/dimensions, one or more optical images, one or more infrared images, an impedance/hydration measurement, one or more additional MR techniques, demographic information, and/or family history. Moreover, the system may catalog or index the invariant MR signature, the additional information and/or an identifier of the tissue sample in the data structure (such as a unique identifier for the tissue sample, e.g., label information) into a large data structure or knowledge base of invariant MR signatures from multiple tissue samples (which is sometimes referred to as a 'biovault') for subsequent use. Note that the system can screen symptomatic and/or asymptomatic biological samples. (In some embodiments, the biological samples are not solely healthy or unhealthy. For example, a particular invariant MR signature may be healthy in certain contexts, such as for a particular person, but may be unhealthy in another context.) Thus, the system can be used to characterize healthy tissue, as well as disease or pathology.

FIG. 1 presents a block diagram illustrating an example of a system 100. This system includes: an MR scanner 110 and computer system 114. As described further below with reference to FIG. 12, computer system 114 may include: a networking subsystem (such as an interface circuit 116), a processing subsystem (such as a processor 118), and a storage subsystem (such as memory 120). During operation of system 100, a technician or an MR operator can scan in information about a tissue sample 112 using sample-information reader (SIR) 122 to extract information (such as an identifier, which may be a unique identifier) from a label associated with tissue sample 112. For example, sample-information reader 122 may acquire an image of the tissue-sample label, and the information may be extracted using an optical character recognition technique. More generally, note that sample-information reader 122 may include: a laser imaging system, an optical imaging system (such as a CCD or CMOS imaging sensor, or an optical camera), an infrared imaging system, a barcode scanner, an RFID reader, a QR code reader, a near-field communication system, and/or a wireless communication system.

Alternatively, the technician or the MR operator may input information about tissue sample 112 via a user interface associated with computer system 114. Note that the extracted and/or input information may include: the unique identifier of tissue sample 112, a subject (or patient) identifier, a subject age, a subject gender, an organ tissue sample 112 was taken from, a tissue type, a date tissue sample 112 was acquired/sampled, a procedure during which tissue sample 112 was acquired, a doctor or practitioner who acquired tissue sample 112, the time and place where tissue sample 112 was removed, a type of tissue sample 112 (such as formalin fixed-paraffin embedded or FFPE, or non-FFPE), a biopsy or diagnosis (if available), etc.

Then, the technician or the MR operator can place tissue sample 112 in MR scanner 110, and can initiate the determination of an invariant MR signature (which may involve MRF, MRT, MRE, MRS, magnetic-field relaxometry, etc.) and/or other measurements, e.g., by pushing a physical button or activating a virtual icon in a user interface associated with computer system 114. Note that the same tissue sample (and, more generally, the same material) can have different MR signals (such as different signal intensities and/or frequencies) in different datasets that are measured in the same MR scanner or in different MR scanners. In general, such measurement-to-measurement variation depends on many factors, including: the particular instance of MR scanner 110, a type or model of MR scanner 110, a set-up of MR scanner 110, the scanning instructions (such as the magnetic-field strengths and the pulse sequences that are applied to tissue sample 112, the MR techniques, the regions of interest in tissue sample 112, one or more voxel sizes and/or the types of nuclei), a detector in MR scanner 110, etc.

These challenges are addressed in system 100 by using the characterization technique to determine the invariant MR signature of tissue sample 112, which is independent of (or has significantly reduced sensitivity to) variations in the magnetic-field strength (and, thus, magnetic-field inhomogeneity). This invariant MR signature may include the information found in or corresponding to the information in an MR fingerprint of tissue sample 112 (such as high-quality quantitative maps of $T_1$, $T_2$, nuclei density, diffusion, velocity/flow, temperature, and magnetic susceptibility). Moreover, the invariant MR signature may be corrected for measurement-to-measurement variation (including variation that occurs from one MR scanner to another). Alternatively, the invariant MR signature may include information that corrects for measurement-to-measurement variation and/or that allows a version of an MR fingerprint to be generated for particular measurement conditions, such as: a particular MR scanner, a particular model of the MR scanner, scanning instructions, a particular detector, etc. Thus, in conjunction with characteristics of a particular MR scanner (such as the model of this particular MR scanner, the scanning instructions, the detector, noise characteristics of the particular MR scanner, magnetic-field inhomogeneity in the particular MR scanner), the invariant MR signature may be used to generate a version of an MR fingerprint as if it were measured by the particular MR scanner. Note that the noise characteristics of the particular MR scanner may depend on the pulse sequence used.

In some embodiments, the invariant MR signature includes parameters in an MR model of voxels in tissue sample 112. Because each voxel in the MR model may include multi-dimensional data on the volumetric density of certain chemical signatures and atomic nuclei, system 100 may determine the invariant MR signature of tissue sample 112 based on an awareness of the region of the body where tissue sample 112 originated or the source of tissue sample 112. Moreover, system 100 may use this information or knowledge about tissue sample 112 to further optimize the scanning instructions (and, more generally, the conditions during the MRF) when collecting MR signals from tissue sample 112. For example, the extracted and/or input information about tissue sample 112, as well as additional stored information in memory 120 that is accessed based on the unique identifier (such as a medical record or medical history that is linked or queried based on the unique identifier), may be used by computer system 114 to determine the scanning instructions (such as different pulse sequences and/or different magnetic-field strengths, e.g., a range of magnetic-field strengths, including 0 T, 6.5 mT, 1.5 T, 3 T, 4.7 T, 9.4 T, and/or 15 T, the MR techniques, the regions of interest in tissue sample 112, the voxel sizes and/or the types of nuclei), the other measurements to perform and, more generally, a scan or analysis plan. In general, the scanning instructions may specify more than a single value of the magnetic-field strength. For example, the scanning instructions may provide or specify a function that describes how the magnetic field will change over time and in space, or multiple functions that specify a 'surface' that can be used to determine the invariant MR signature of tissue sample 112. As described further below with reference to FIG. 2, in some embodiments the magnetic field is physically and/or virtually manipulated to achieve the specified surface. In particular, the magnetic field may be rotated as a function of time, or in embodiments with physically separate ring magnets that generate the magnetic field, the magnetic field may be changed by: changing the physical distance between the ring magnets, changing the orientation of one ring magnet with respect to the other ring magnet, moving a ring magnet along the z axis, etc.

Moreover, as described further below, note that the other measurements may include: impedance measurements, optical imaging, scanning of dimensions of tissue sample 112, weighing tissue sample 112 and/or other tests that may be included in the characterization technique. For example, a gel-covered table in MR scanner 110 can be used to measure an impedance of tissue sample 112 and/or a weight of tissue sample 112. In some embodiments the other measurements probe tissue sample 112 non-destructively (e.g., using electromagnetic or mechanical waves). However, in other embodiments destructive testing or testing that permanently modifies tissue sample 112 is used. This may allow integrated therapeutics or even, in some embodiments, the ability to collect more information. Thus, the characterization technique may include non-destructive and/or destructive measurement techniques, as well as therapies such as: proton beam therapy, radiation therapy, magnetically guided nano particles, etc.

In addition, predetermined characterization of MR scanner 110 may be used to determine the scanning instructions. Alternatively, if MR scanner 110 has not already been characterized, system 100 may characterize and store characteristics of MR scanner 110 prior to determining the invariant MR signature, so that the characteristic of MR scanner 110 can be used during the characterization technique, such as to determine the scanning instructions. For example, during operation, computer system 114 may characterize MR scanner 110 based on scans of a phantom.

Note that the predetermined characterization of MR scanner 110 may include a mapping or determination of the inhomogeneity of the magnetic field of MR scanner 110 (because the inhomogeneity may depend on the magnetic-field strength, measurements may be performed at different magnetic-field strengths). The predetermined characterization may also include environmental, geographical and/or other parameters. For example, RF pulses generated by a pulse generator in system 100 may vary from one MR scanner to another, and may vary as a function of time because the performance of components may depend on parameters such as: the load, the temperature, the MR coil configuration, amplifiers, humidity, magnetic storms and/or geolocation. Consequently, in addition to MR signals, the RF pulses may be measured, e.g., using a signal splitter between an RF pulse generator and an RF (transmission) coil in MR scanner 110. In some embodiments, the magnetic field produced by the RF coil is measured using a test coil. Note that, because a specific pulse sequence may correspond to a specific voxel size, different pulse sequences corresponding to different voxel sizes may be used when characterizing MR scanner 110 and/or when determining the scanning instructions.

Figure 3:
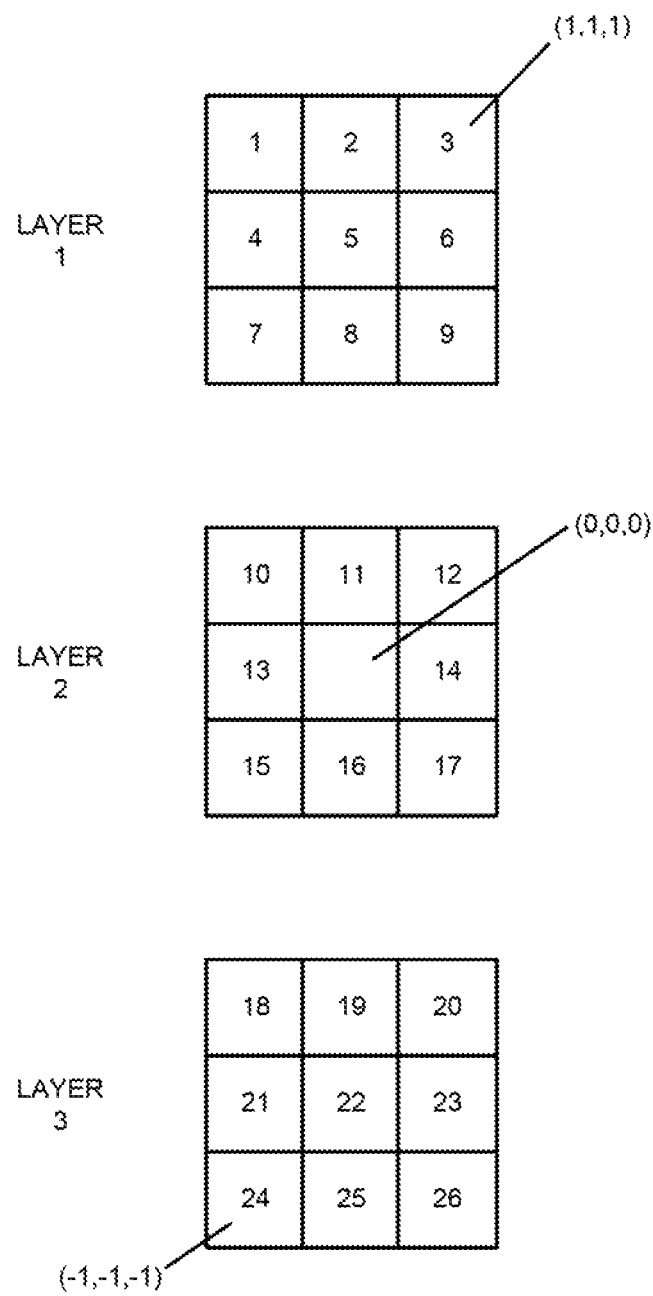
FIG. 3 is a drawing illustrating the determination of an MR model in accordance with an embodiment of the present disclosure.

As described further below with reference to FIG. 3, the measurements and recorded signals associated with MR scanner 110 may be used to generate an MR model of MR scanner 110 that accurately predicts MR signal evolution or response for a phantom having known properties over a range of parameters ($T_1$, $T_2$, proton density, off-resonances, environment, location, temperature, pulse sequences, etc.) using the Bloch equations, full Liouvillian computations or another simulation technique. In this way, the MR model may characterize MR scanner 110.

The predetermined characterization of MR scanner 110 can be used to transform a generic invariant MR signature into a machine-specific invariant MR signature associated with a particular MR scanner, such as MR scanner 110. In conjunction with the magnetic field and the pulse sequence, the machine-specific invariant MR signature may be used to predict MR signals during an arbitrary MR scan in the particular MR scanner. Similarly, predetermined characterizations of different MR scanners can be used to convert from one machine-specific invariant MR signature to another.

In some embodiments, the predetermined characterization of MR scanner 110 includes measured ambient noise from electronics in or associated with MR scanner 110. During subsequent MR scans or simulations, digital filters may use the measured noise (or statistical parameters that describe the measured noise) to improve the quality of measured MR signals and/or calculated MR models. Moreover, the various measurements may be synchronized with an external reference clock or to a biological time period (such as a respiration period, a heart-beat period, a fundamental period for body motion, etc.) to enable subsequent synchronous averaging or additional signal processing.

Moreover, during the characterization technique, computer system 114 may repeatedly perform MR scans of different materials (such as different types nuclei) in tissue sample 112 using MR scanner 110 based on instances of the scanning instructions that are received via network 132. Note that the MR scans of the different materials may be pseudorandomly acquired. For example, an MR scan of a particular material in tissue sample 112 may be selected based on a random or a pseudorandom number provided by a circuit or software-implemented random or a pseudorandom number generator in computer system 114. Alternatively, the different materials in tissue sample 112 may be systematically scanned for each instance of the scanning instructions.

Furthermore, the MR signals acquired or captured during a particular MR scan may be used to modify or adapt an MR model of voxels in tissue sample 112. For example, as noted previously and as described further below with reference to FIG. 3, computer system 114 may determine the MR model (such as parameters in the MR model) based on differences (or a difference vector) between MR signals associated with the voxels in one or more MR scans and simulated MR signals (which may be generated using the MR model, an instance of the scanning instructions and optionally the characteristics of MR scanner 110). Note that the difference vector may be weighted based on a priori computed information to reduce the error, e.g., to obtain the smallest difference vector or the smallest difference vector measured across a set of weighted simulated MR signals (which may be precomputed). In some embodiments, the difference vector is determined using a dot product or inner product of one or more MR signals and simulated MR signals (which are each associated with or corrected to a common magnetic-field strength), cosine similarity between one or more MR signals and simulated MR signals, spectral analysis, and/or another comparison technique.

Then, based on the remaining differences (or the remaining difference vector) the scanning instructions may be modified, i.e., a new instance of the scanning instructions (including one or more magnetic-field strengths and one or more pulse sequence(s) that will be applied to tissue sample 112, the MR technique, the regions of interest in tissue sample 112, the voxel sizes and/or the types of nuclei) may be determined. These operations may be iteratively repeated until a convergence criterion is achieved. For example, the convergence criterion may include that the difference between the MR signals and the simulated MR signals is less than a predefined value (such as 0.1, 1, 3, 5 or 10%) and/or that the changes to the scanning instructions are less than the predefined value.

Figure 2:
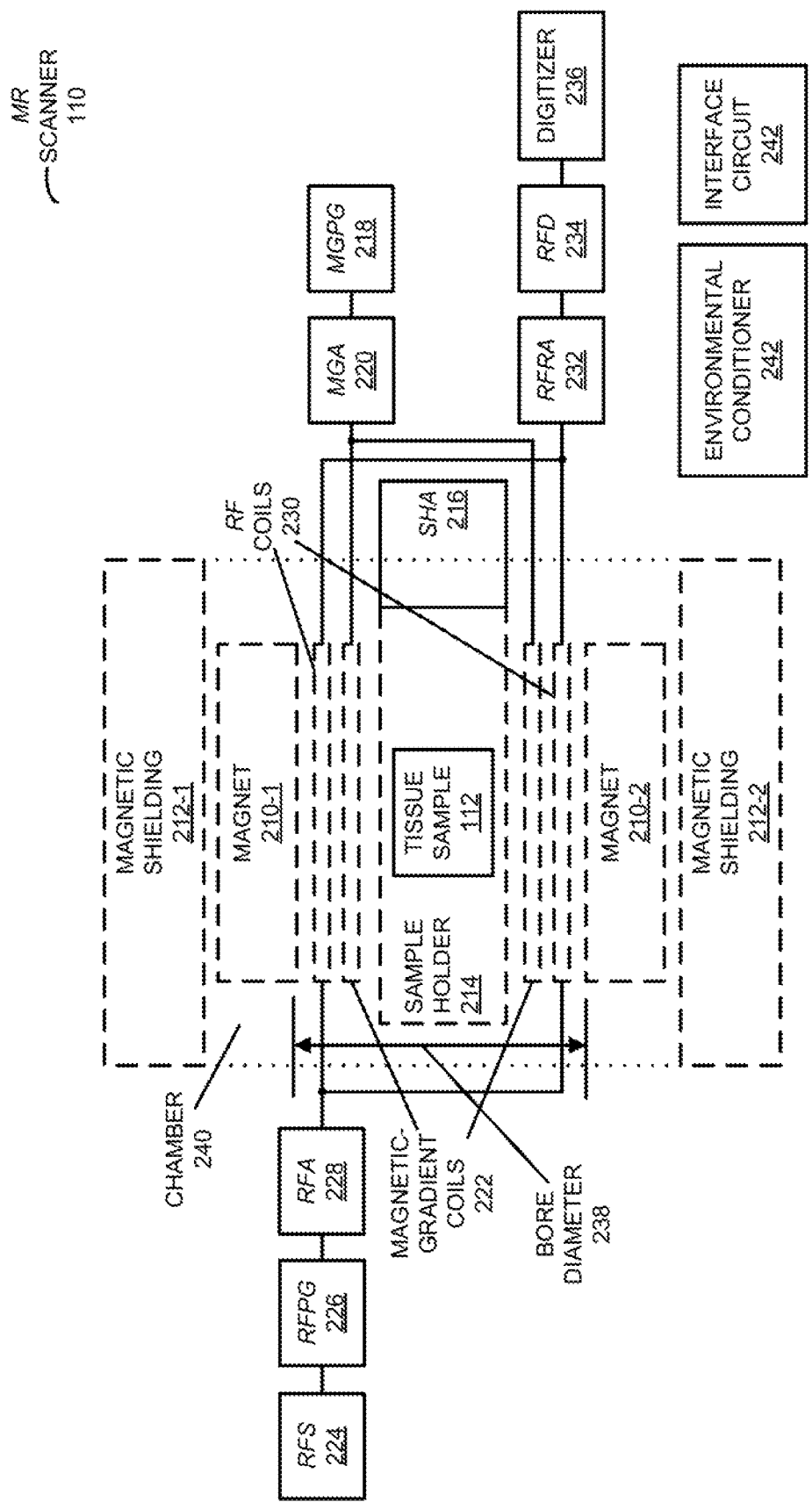
FIG. 2 is a block diagram of the MR scanner in the system of FIG. 1 in accordance with an embodiment of the present disclosure.

We now further describe the operations in the characterization technique in more detail. FIG. 2 presents a block diagram of an example of MR scanner 110. This MR scanner may include a magnet 210, magnetic shielding 212, a sample holder 214, a sample-holder articulator (SHA) 216, a magnetic-gradient pulse generator (MGPG) 218, a magnetic-gradient amplifier (MGA) 220, magnetic-gradient coils 222, an RF pulse generator (RFPG) 226, an RF source (RFS) 224, RF amplifier (RFA) 228, RF coils 230, an RF receive amplifier (RFRA) 232, an RF detector (RFD) 234, a digitizer 236 (such as an analog-to-digital converter), an environmental conditioner 242 and an interface circuit 244. (Note that mechanical and electrical connections to environmental conditioner 242 and interface circuit 244 are not shown in FIG. 2.) At least some of these components may be coupled, via interface circuit 244, network 132 (FIG. 1) and interface circuit 116 (FIG. 1), to computer system 114, which may control operation of MR scanner 110. The components in MR scanner 110 are described briefly below.

Note that MR scanner 110 may be a closed-bore or an open-bore system. In particular, magnet 210 (illustrated in a cross-sectional view in FIG. 2 by portions of magnet 210-1 and 210-2) may be closed bore or open bore. For example, a bore diameter 238 of magnet 210 may be between 1 and 10 cm or between 5 and 30 cm. An open-bore system may generate a magnetic field using two plates separated by a gap, and tissue sample 112 may be exposed to (and nuclei in tissue sample may be polarized by) the magnetic field between the plates. Alternatively, a closed-bore system may have a toroidal shaped magnet 210, tissue sample 112 may be moved through a hole in the center of the toroid (thus, using a strong field or high field to polarize nuclei in tissue sample 112). Moreover, the orientation of magnet 210 may be horizontal (which is sometimes referred to as 'horizontal bore') so that tissue sample 112 moves horizontally through the magnetic field, but can also be vertically oriented. In general, MR scanner 110 may scan tissue sample 112 in various positions, including at different angles, orientations and perspectives (e.g., by adjusting sample-holder articulator 216). (Thus, when MR scans are performed on individuals or animals, MR scanner 110 may allow measurements to be made while a subject is standing, sitting or laying down.) Note that embodiments with a smaller bore diameter 238 may allow MR scanner 110 to be portable.

Depending on the MR technique, the magnetic-field strength $B_0$ of magnet 210 may be low field (e.g., an electromagnet having a peak magnetic-field strength that is less than 0.1 T, such as a magnetic-field strength as low as 0.001 T or even 0 T), a strong field (e.g., a ferro-magnet having a peak magnetic-field strength of around 0.5 T) or high field (e.g., a superconducting magnet having a peak magnetic-field strength greater than around 0.5 T). In general, a wide variety of magnets and magnetic configurations may be used. In embodiments with a superconductor, magnet 210 may be cooled using a cryogenic fluid, such as liquid helium or liquid helium in a surrounding dewar filled with liquid nitrogen or that is refrigerated. However, in other embodiments magnet 210 operates at or near room temperature. Furthermore, magnet 210 may be modular, such as a set of superconducting rings that each have a peak magnetic-field strength of 0.5 T and that can be added, removed or moved to create different magnetic-field magnitudes and configurations.

Magnet 210 may produce magnetic fields that can be changed physically and/or virtually (via gradient fields and/or pulse sequences). This capability may allow slow rotation of the main external magnetic field, so that MRS can be performed at low magnetic-fields strengths. This additional degree of freedom may provide more ways to perturb the magnetic moments in tissue sample 112 to obtain information that can reduce the complexity of the invariant MR signature calculations. Note that moving or changing the orientation of magnet 210 may involve: moving pairs of ring magnets closer or further away on the z axis as part of a scan plan; rotating magnet 210 relative to the volume of space being indexed; changing the orientation/alignment of magnet 210 with respect to the z axis of the volume being indexed, etc. Moreover, 'physically' can mean physical movement of magnet 210, while 'virtually' may indicate that gradient fields and/or pulse sequences (such as a so-called 'spin-lock technique') are used to achieve the same result without physically changing the orientation of magnet 210. In general, these techniques may be used independently of each other or two or more of the techniques may be used in conjunction with each other.

Magnet 210 may also be used to (intentionally) dynamically vary the magnetic-field inhomogeneity. For example, by physically rotating a shim coil and/or by applying particular pulse sequences, the magnetic-field inhomogeneity may be modified. Moreover, by introducing specific kinds of magnetic-field inhomogeneity at different points in space, MR scanner 110 can differentiate certain kinds of tissue that are in close proximity.

Magnetic shielding 212 may include steel plates or metal sheets of silicon steel. This magnetic shielding may be placed all around a room, fully covering walls, floors and ceilings, in order to attenuate the magnetic-field strength outside the room to below 5 Gauss (or 0.5 mT). Moreover, special doors and doorframe seals may be used to further reduce the magnetic field that 'leaks' out of the room. Furthermore, magnet 210 may include shielding (such as a second set of superconducting windings with an opposite current flow than the main superconducting windings) in order to reduce the fringe magnetic field. For example, the magnetic-field strength may be 0.5 mT at a distance of four meters from magnet 210. This configuration may reduce the amount of magnetic shielding 212 or may eliminate the need for magnetic shielding 212 entirely.

In some embodiments, magnetic shielding 212 may provide a chamber 240 (defined by a surface of magnetic shielding 212), and this chamber may be optionally sealed so that tissue sample 112 is at less than atmospheric pressure (i.e., a vacuum chamber) or contains an inert gas (such as xenon) that can be pre-polarized to improve the MR imaging quality. (More generally, a solid, liquid or gas contrast agent may be used to improve the MR imaging quality.) In particular, environmental conditioner 242, such as a gas valve and a vacuum pump that are controlled by computer system 114, may be used to reduce the pressure in chamber 240. Alternatively, environmental conditioner 242 may include the gas valve and a gas tank that selectively allow (under control of computer system 114) the inert gas to flow into chamber 240. However, in other embodiments chamber 240 is defined by or provided by a surface of sample holder 214.

Note that magnetic-gradient pulse generator 218 may provide gradient pulses. These gradient pulses may be amplified by magnetic-gradient amplifier 220 to a level suitable for driving magnetic-gradient coils 222. Note that magnetic-gradient pulse generator 218 and magnetic-gradient amplifier 220 may be controlled by computer system 114 via an interface circuit 116 (FIG. 1), network 132 (FIG. 1) and interface circuit 244. For example, computer system 114 may specify the types and shapes of magnetic pulses provided by magnetic-gradient pulse generator 218, and may specify the amplification or gain of magnetic-gradient amplifier 220.

Moreover, magnetic-gradient coils 222 may produce the shape and amplitude of the gradient magnetic field along the x, y and z axes (in a right-handed Cartesian coordinate system). Magnetic-gradient coils 222 typically operate at room temperature and may produce spatial gradients in the magnetic field $B_0$. For example, in a horizontal bore system, a gradient in the magnetic field $B_0$ along the z-axis or direction (i.e., parallel to a symmetry axis of the bore of magnet 210) may be achieved using an anti-Helmholtz coil, with current in each coil adding to or subtracting from the magnetic field $B_0$ to achieve the gradient. Furthermore, gradients along the x and y-axes may be generated or created using a pair coils having a 'figure 8' shape (which create gradients along their respective axes).

In some embodiments, magnetic-gradient coils 222 have gradients of 100 mT/m and have fast switching times (or slew rates) of 150 T/m/s, which may enable a slice thickness of 0.7 mm and a voxel resolution of 0.1 mm in 3D imaging. However, by using high frequencies (such as frequencies above approximately 100 kHz), slew rates higher than the current U.S. slew-rate limit of 200 T/m/s may be used. If magnet 210 produces a larger magnetic-field strength (such as 7 T), an isometric voxel resolution of 60 μm may be achieved.

Furthermore, RF pulse generator 226 may generate RF pulses based on carrier waves output by RF source 224 (such as sinewaves or RF pulses having desired fundamental frequencies based on a target type of nuclei and magnetic-field strength $B_0$), and RF amplifier 228 may increase the power of the RF pulses to be strong enough to drive RF coils 230 (e.g., increasing the power from milliWatts to kiloWatts). RF coils 230 may create a magnetic field $B_1$ that rotates the net magnetization of type of nuclei in tissue sample 112 based on the pulse sequence. Note that RF pulse generator 226, RF source 224 and RF amplifier 228 may be controlled by computer system 114 via interface circuit 116 (FIG. 1), network 132 (FIG. 1) and interface circuit 244. For example, computer system 114 may specify the type or shape of pulse(s) output by RF pulse generator 226, the frequencies in the carrier frequencies or pulses provided by RF source 224 and/or the amplification or gain of RF amplifier 228.

In some embodiments, RF pulse generator 226 shapes the carrier waves or RF pulses into apodized sinc pulses, which may smooth discontinuities that can adversely affect the measurements and/or subsequent signal processing (such as a Fourier transform). Apodized sinc pulses may excite the spin states of the nuclei, and these excited spin states may decay and release a pulse of RF energy that is captured during acquisition. In general, a wide variety of pulse sequences may be used during the characterization technique. For example, the pulse sequence may include or may be associated with MR techniques such as: turbo field echo (TFE), fast field echo (FFE), susceptibility weighted imaging (SWE), short tau inversion recovery (STIR) or short $T_1$ inversion recovery (a type of suppression technique for fatty tissue with an inversion time TI equal to $T_1 \cdot \ln(2)$ so that the MR signal of fat is zero), turbo spin echo (TSE), fast low angle shot or FLASH (a type of spin-echo sequence in which larger tip angles provide more $T_1$-weighted images and smaller tip angles provide more $T_2$-weighted images), volumetric interpolated brain examination (VIBE), magnetic pulse rapid gradient echo (MP RAGE), fluid attenuation inverted recovery (FLAIR), a parallel imaging technique such as sensitivity encoding (SENSE), or another pulse sequence. Note that SENSE may involve: generating coil sensitivity maps, acquiring partial k-space MR data, reconstructing partial field of view images from each of RF coils 230, and combining the partial field of view images using matrix inversion. Moreover, the pulse sequence may include or may be associated with second and third generation parallel imaging techniques, such as GRAPPA, Auto-Smash or VD-SMASH, which are imaging techniques that speed up MRI pulse sequences using k-space undersampling, and the acquisition of additional lines provides a form of calibration because the coefficients of MR signals across RF coils 230 can be determined from the measurements. Furthermore, the pulse sequence(s) may be designed or selected to be independent of the hardware or MR scanner. For example, a pulse sequence may be designed or selected to cancel noise and amplify specific parameters of interest (which is sometimes referred to as 'quantum pumping'). (These pulse sequences may be used in NMR or MRI to quantify certain parameters in a machine-independent manner). As described below, quantum pumping may be used an alternative to pseudorandom pulse sequences.

Thus, in general, the pulse sequences may include: existing pulse sequences (when accurate measurements and simulations of the properties of the MR scanner can be obtained so that invariant MR signatures can be determined); pseudorandom pulse sequences (which may also involve accurate measurement and simulation of noise, but the pseudorandom nature may help to create more unique Bloch trajectories at each point in space); and/or quantum pumping (which may, at least in part, cancel out MR scanner-dependent noise, and thus, may simplify or reduce the required accuracy of the simulations used to determine the invariant MR signatures).

RF coils 230 also may detect the transverse magnetization as it precesses in the xy plane. In general, a given one of RF coils 230 may be transmit only, receive only or can transmit and receive RF signals. Moreover, RF coils 230 may be oriented such that the magnetic field $B_1$ is perpendicular to the magnetic field $B_0$. Furthermore, RF coils 230 may be tuned to the Larmor frequency (e.g., the resonant frequency of a type of nuclei being imaged or measured at the magnetic field $B_0$), e.g., by adjusting a capacitor or an inductor, or changing its capacitance or inductance (such as by using matching and tuning capacitors). Note that RF coils 230 may include: an Alderman-Grant coil, a bird cage (which may be used for volume measurements), a butterfly coil, a dome resonator, a gradiometer, an implantable coil, an inside out/Schlumberger coil, an intravascular coil, a ladder coil, a Litz coil, a loop-gap resonator coil, a loop-stick coil, a meanderline coil, a mouse coil, a multi-turn solenoid coil, a phased-array coil, a phased-array volume coil, a ribbonator coil, a saddle coil, a scroll coil, a single-turn solenoid coil (which may be used for extremity measurements), a spiral coil, a surface coil (which may be used for receiving body or volume signals because they have a good signal-to-noise ratio for tissues and samples adjacent to the coil), a superconducting coil, a transmission-line coil, a truncated-spiral coil, a 3-axis coil, and/or a wide-band RF coil (which may be used to simultaneously excite multiple spectra).

In some embodiments, one or more of RF coils 230 includes a thermal imaging sensor, which can include a forward looking infrared (FLIR) sensor. The one or more thermal imaging sensors can be attached modularly (e.g., snapped together in concentric shells, snapped on additions, assembled with interlocking interfaces, etc.) and can communicate with each other via wireless or wired communication. Moreover, in some embodiments surface coils that can be controlled by software on computer system 114 that executes the scan plan allow certain modalities or MR techniques to be turned on and off in real-time as the analysis of tissue sample 112 progresses. For example, this approach may allow MRE to be performed on an anomaly, or a thermal image to be acquired of tissue sample 112 or the surrounding region. In these embodiments, RE coils 230 can be constructed to include multiple sensors and data-collection equipment to facilitate specialized anomaly detection. Thus, RF coils 230 may be optimized for parallel collection of data using: MRF, MRT, MRS, MRE, multi-nuclear imaging of two or more nuclei (such as $^1$H, $^{23}$Na, $^{31}$P, $^{13}$C, $^{19}$F, $^{39}$K, $^{43}$Ca, etc.), diffusion tensor imaging, N-channel scanning, magnetic-field relaxometry, etc.

In some embodiments, MR scanner 110 includes non-inductive sensing technologies in addition to or instead of RF coils 230, such as a magnetometer, a superconducting quantum interference device, etc. Note that non-inductive sensors may enable sweeping of the magnetic field generated by magnet 210 without requiring that RF coils 230 be tuned to different frequencies corresponding to the magnetic-field strengths.

The RF signals received by RF coils 230 may be amplified by RF receive amplifier 232 and detected using RF detector 234. In particular, RF detector 234 may capture or demodulate the RF signals to baseband. For example, RF detector 234 may measure MR signals in their simplest form, such as the free-induction decay of excited spin states, though it is possible to receive many more complicated pulse sequences. Computer system 114 may control RF detector 234 via interface circuit 116 (FIG. 1), network 132 (FIG. 1) and interface circuit 244. For example, computer system 114 may specify which MR (or RF) signals to capture.

Note that RF detector 234 may be a linear analog detector, a quadrature analog detector or a heterodyne receiver. Linear analog detectors may capture MR signals along one vector in the coordinate space (e.g., the magnetization along the x or y axis), and a quadrature analog detector may simultaneously capture MR signals along two vectors in the coordinate space (e.g., the magnetization along the x and the y axis. In some embodiments, a linear analog detector includes a doubly balanced mixer, and a quadrature analog detector includes a pair of double balanced mixers, a pair of filters, a pair of amplifiers and a 90° phase shifter.

Furthermore, digitizer 236 may digitize the MR signals received by the RF detector 234. For example, digitizer 236 may use a 1 MHz sampling frequency. While this may oversample the MR signal, digital filtering (such as filtering using by multiplying by a bandpass filter in the frequency domain or convolving using a sinc function in the time domain) may be used to capture the desired frequencies and to remove higher frequency signals. In the process, the amount of data to be processed and stored by computer system 114 may be reduced to a more manageable level. However, in general, a variety of sampling frequencies greater than twice the Nyquist frequency may be used. For example, there may be up to 1000 samples per MR signal so that a frequency resolution of at least 500 Hz can be achieved. Computer system 114 may control digitizer 236 via interface circuit 116 (FIG. 1), network 132 (FIG. 1) and interface circuit 244. In particular, computer system 114 may specify the sampling rate and/or filter settings used by digitizer 236.

After digitizing, computer system 114 (FIG. 1) may perform a variety of digital signal processing (such as filtering, image processing, etc.), noise cancellation and transformation techniques (such as a discrete Fourier transform, a Z transform, a discrete cosine transform, data compression, etc). In general, the MR signal may specified in the time domain and/or the frequency domain. Thus, in some embodiments, the MR signal is represented in k space.

In one embodiment, the readings from RF coils 230 are digitized within or just outside of the coil assembly and transmitted wirelessly to computer system 114 to avoid messy cable tangling, and without creating significant RF noise in the frequencies of interest. For example, the data may be transmitted to computer system 114 at lower or higher frequencies than the Larmor frequencies of targeted nuclei in tissue sample 112, which may allow the data to be filtered to exclude noise artifacts. Furthermore, in some embodiments RF coils 230 are tuned to receive one or more frequencies. For example, depending on the spectra desired, a wide-band receiver coil can be used or a software or hardware-based tuner can be used to automatically tune at least one of RF detector 234 to receive one or more frequencies from a desired nuclei or molecule. (However, as noted previously, in other embodiments an un-tuned receiver, such as a magnetometer, is used.) Additionally, in embodiments where parallel imaging techniques are used, different parts of surface coils on tissue sample 112 operate in parallel to concurrently or simultaneously capture different spectra.

Note that sample holder 214 may support tissue sample 112 while tissue sample 112 is moved through the magnetic fields and measured by MR scanner 110. Moreover, as noted previously, sample-holder articulator 216 may articulate or move sample holder 214 as needed to position tissue sample 112 in relation to the magnetic fields generated by magnet 210 and magnetic-gradient coils 222. In particular, sample-holder articulator 216 may rotate tissue sample 112 in 2D or 3D while tissue sample 112 is being measured by MR scanner 110 based on instructions received from computer system 114 via interface circuit 116 (FIG. 1), network 132 (FIG. 1) and interface circuit 244. Furthermore, as noted previously, sample holder 214 may be enclosed in chamber 240 or may be an enclosed chamber, including a sealed chamber that can be pumped down to reduced pressure using a vacuum pump or flooded with an inert gas. In some embodiments, because environmental conditions can have an effect on tissue sample 112, sample holder 214 includes sensors that measure temperature, humidity, pressure, another environmental condition, etc. inside the room, inside chamber 240 that contains sample holder 214, or inside sample holder 214.

In some embodiments, sample holder 214 includes a tube (or a vessel) and sample-holder articulator 216 includes one or more air jets. These air jet(s) can be used to manipulate the position of tissue sample 112. For example, the tube can be made of glass (such as optically clear or transparent glass), Teflon (which may be transparent at other frequencies of electromagnetic radiation), or another suitable material. Moreover, the tube may include features on its outer surface (such as a texture, fins or other features) that enable tissue sample 112 to be articulated or manipulated into different positions using a gripping or interlocking interface to a motor or robotic arm, thereby allowing system 100 (FIG. 1) to re-orient tissue sample 112 during the indexing or sample-measurement process.

Moreover, the tube may be inserted into a multi-axis magnet, such as a multi-axis magnet provided by Cryomagnetics, Inc. of Oak Ridge, Tenn. Then, system 100 (FIG. 1) can probe or measure tissue sample 112 from multiple directions, angles, perspectives and alignments without requiring multiple sensors around bore 236. For example, tissue sample 112 may be rotated, and a single camera, CCD or CMOS sensor can capture multiple photographs of tissue sample 112 so that some or all of tissue sample 112 may be captured, thereby reducing the cost and complexity of system 100, and improving the reliability. Furthermore, the tube may provide the chamber that is under vacuum or that is filled with an inert pre-polarized gas to increase the resolution. In some embodiments, a low-cost and portable chip-scale device (such as a microfluidic chip) is used to produce the polarized or magnetized gas, so that faint MR signals can be detected. For example, as noted previously, polarized xenon can be used as a contrast agent to enhance images in MRI of, e.g., human lungs. The polarized xenon atoms may be produced in the chip by collisions with rubidium atoms that are illuminated with circularly polarized light. Then, the polarized xenon may flow out of the chip and may be directed into the tube or chamber 240.

Referring back to FIG. 1, computer system 114 may instruct one or more optional measurement devices 124 to perform other measurements on tissue sample 112 to obtain physical property information that specifies a measured physical property of tissue sample 112, which may be used to determine a diagnostic classification of tissue sample 112 and/or which may be included in metadata associated with tissue sample 112. For example, the one or more optional measurement devices 124 may include: a medical grade scale that determines a weight of tissue sample 112; a measurement device that measures one or more dimensions of tissue sample 112 (such as: a laser imaging system, an optical imaging system, an infrared imaging system, and/or a spectroscopy system); a light source that can selectively illuminate tissue sample 112 and a camera-enabled microscope that acquires or measures one or more optical images of tissue sample 112 at one or more perspectives, orientations or lighting conditions; and/or a bioelectric impedance analyzer that performs a multi-lead measurement of an impedance of tissue sample 112 at DC or an AC frequency (and which may correspond to hydration of tissue sample 112, and thus may be used to determine or compute the hydration of tissue sample 112 or the subject that tissue sample 112 was taken from). Alternatively, the hydration or hydration level, which can affect tissue sample 112, and thus the invariant MR signature, may be measured directly. In some embodiments, the other measurements on tissue sample 112 include: cell cytology, genetic sequencing (such as sequencing some or all of the DNA in the genome, RNA sequencing or transcriptomics, gene expression, etc.), protein analysis or proteomics (e.g., using mass spectrometry, liquid chromatography and/or NMR), lipidomics (and, more generally, microbolomics), computed tomography, electron-spin resonance (which may be used to measure free radicals), x-ray imaging, ultrasonic imaging (e.g., ultrasound), photo-acoustic imaging, infrared imaging or infrared spectroscopy, other non-destructive measurements (such as radar or millimeter-wave scanning), activity data for a subject (such as data capture using a wearable electronic device), measurements performed by nano particles in tissue sample 112, chemical composition of fluids (such as blood) measured at arbitrary locations in tissue sample 112 (or an individual) non-destructively or by drawing a blood sample (e.g., using microfluidics), etc. Alternatively, computer system 114 may access data for some or all of these other measurements that are stored in a remote data structure based on the unique identifier for tissue sample 112.

Note that the weight and the dimensions of tissue sample 112 may be used to calculate its density. Moreover, the one or more optional measurement devices 124 may acquire images of individual cells for inspection and pathology identification. Furthermore, the medical grade scale may provide information about the chemical composition and hydration levels of tissue sample 112 if tissue sample 112 is weighed: immediately upon excision, months after excision, before and after an FFPE process, and/or before and after the MR scanning (or other imaging operations). In some embodiments, measuring tissue sample 112 in different portions of the electromagnetic spectrum may allow a correction for susceptibility artifacts that may not show in in optical or infrared scans, but that can occur in certain radio scans.

In some embodiments, system 100 includes an optional wave generator 126 that is controlled by computer system 114 via interface circuit 116. This optional wave generator may generate ultrasonic waves (and, more generally, mechanical waves) that are applied to tissue sample 112 during MRE to measure a stiffness of tissue sample 112. For example, optional generator 126 may generate waves at one or both ends of bore 236 (FIG. 2) of MR scanner 110 or may direct waves at one of both ends of bore 236 (FIG. 2) of MR scanner 110 using a waveguide, such that tissue sample 112 receives the ultrasonic waves. In some embodiments, the ultrasonic waves include sheer waves. MR scanner 110 may acquire quantitative MR fingerprints or images of the propagation of the shear waves through tissue sample 112, and may process the images of the shear waves to produce a quantitative mapping of the tissue stiffness.

If tissue sample 112 is formalin fixed-paraffin embedded, after the invariant MR signature is determined computer system 114 may transform the determined invariant MR signature so that it approximates an in-vivo tissue (i.e., without the formalin or the paraffin. For example, on a voxel-by-voxel basis, computer system 114 may subtract a predefined or predetermined invariant MR signature of the formalin or the paraffin from the determined invariant MR signature to generate an estimated invariant MR signature. Alternatively, computer system 114 may correct the parameters in the MR model on a voxel-by-voxel basis for the formalin or the paraffin to generate an estimated invariant MR signature. In some embodiments, a partial volume technique is used to subtract out the contribution or the effect of the paraffin or wax at borders of tissue sample 112. In particular, computer system 114 may determine what percentage of a given voxel is paraffin and may remove or subtract out that weighted portion of the invariant MR signature or the MR signals that are used to compute the invariant MR signature.

Furthermore, computer system 114 may store the raw data (such as MR signals from a biological sample, the applied non-ideal pulse sequences, and measured noise), the invariant MR signature(s) and/or other measurements in the biovault, such as in memory 120 (which may be locally and/or remotely located, such as in a cloud-based archive device). In general, the measured information stored in the biovault may be sufficiently encompassing to allow the MR model to be trained based on the scanning instructions and, thus, the invariant MR signature(s) to be determined. Thus, the stored information may include different output signals at different points in the measurement pipeline (e.g., before an amplifier, after the amplifier, etc.), environmental conditions, geographic location, etc. The stored information may facilitate accurate simulations of an MR scan and the tissue sample, e.g., by training an MR model.

The stored information may include or may be associated with the unique identifier or a new unique identifier generated by computer system 114 that facilitates subsequent identification, as well as searching or querying of the biovault. Thus, if tissue sample 112 is subsequently re-measured at a later time, computer system 114 may store the results or differential results (such as any changes in the invariant MR signatures) so that changes since the last measurements can also be used for searching. Moreover, the stored information may include information about the time, location and/or system parameters (such as information that specifies or identifies MR scanner 110) when tissue sample 112 was measured. Note that the stored information may be encrypted. For example, symmetric or asymmetric encryption based on an encryption key associated with the unique identifier may be used.

In some embodiments, computer system 114 optionally compares the invariant MR signature of tissue sample 112 to one or more other invariant MR signatures, which may have been previously determined for tissue sample 112 or another tissue sample. (Alternatively, computer system 114 may optionally compare an MR fingerprint calculated from or based on the determined invariant MR signature with one or more predetermined MR fingerprints.) Based on this comparison, computer system 114 may optionally determine a classification of tissue 112, which may be stored in the biovault along with or associated with the unique identifier. Note that the determined or selected classification may be the one that has the lowest chance of being a classification error or the lowest matching error. Furthermore, if there are multiple potential or candidate classifications that have similar estimated classification errors (e.g., based on a predetermined supervised-learning model), then the classification of a given voxel may be determined based on a priori information, e.g., the classifications of nearby voxels or combinations (such as linear combinations) of these neighboring classifications, which may help reduce the classification error of the given voxel.

The ability to track labels or classifications and outcomes over time may allow the system to take an invariant MR signature and look up information that is known about it, such as: how frequently it is found, in which organs, has it been labeled bad or good, in which circumstances was it labeled bad or good, etc. In this way, the metadata about the MR signatures may get richer over time. For example, an individual (or tissue samples from the individual) may be indexed every six months. If cancer occurs during one of these indexing operations, this MR signature may be labeled 'bad.' But what about the classifications of historical MR signatures in that same region of the individual? Does the cancer diagnosis potentially make them pre-cancerous? The system may find enough evidence, based on multiple tissue samples, that the earlier MR signatures are early indictors of cancer and that there is a path through the MR-signature space is characteristic of this pathology evolving over time. Consequently, the biovault may allow such longitudinal and cross-subject analysis to identify such paths, which can be use in subsequent classifications and diagnoses.

Moreover, by comparing longitudinally for a particular subject and/or across subjects within the biovault, the system may be able to solve problems and assist in identifying pathologies without requiring the use of a deterministic machine-learning or supervised-learning model. For example, the system may be able to differentially identify the presence of a foreign object (such as screws, pins, joint replacements, etc.) embedded in a tissue sample or a biological sample even if the biovault does not include or does not have previous knowledge about the foreign object. In particular, a ferromagnetic material may be detected based on the resulting magnetic-field distortion, and the invariant MR signature may include a correction for this magnetic-field distortion.

In some embodiments, the biovault provides the ability to aggregate invariant MR signatures on related tissue samples in other biovaults without these biovaults sharing other information about their tissue samples. This may allow global analytics to be performed on tissue samples in siloed or isolated biovaults.

After tissue sample 112 is measured, system 100 may use an optional vacuum sealer 128 to enclose and seal tissue sample 112 in vacuum in preparation for archival storage. Moreover, in some embodiments, tissue sample 112 is formalin fixed-paraffin embedded after the measurements. Furthermore, a physical or an electronic label may be attached to or associated with tissue sample 112 by an optional labeler 130 to facilitate subsequent identification. The information in the physical or electronic label may include the information input and/or extracted at the start of the characterization technique. In some embodiments, tissue sample 112 is destroyed after measurements are made.

While the preceding discussion illustrated the use of system 100 to scan or index tissue sample 112, in other embodiments system 100 may be used to scan or index multiple tissue samples from the same person or animal, or from different persons or animals. These scans may partially or fully overlap in time (i.e., may, at least in part, occur concurrently or simultaneously) to increase throughput.

Moreover, while the preceding discussion illustrated the technician or the MR operator using system 100, in other embodiments system 100 is highly automated, so that tissue sample 112 may be loaded into MR scanner 110, MR measurements and/or the other measurements may be performed, an invariant MR signature can be determined, information may be stored in the biovault, tissue sample 112 may be removed, and these operations can be repeated for one or more additional tissue samples with minimal or no human action.

We now further describe determination of an invariant MR signature. FIG. 3 presents a drawing illustrating an example of determination of an MR model. The MR model may be a 3D model of voxels in a tissue sample, and may include parameters in the Bloch equations for each of the voxels. In particular, with a quasi-static magnetic field $B_0$ along the z axis, the Bloch equations are $$\frac{dM_x(t)}{dt} = \gamma \cdot (\vec{M}(t) \otimes \vec{B}(t))_x - \frac{M_x(t)}{T_2},$$

$$\frac{dM_y(t)}{dt} = \gamma \cdot (\vec{M}(t) \otimes \vec{B}(t))_y - \frac{M_y(t)}{T_2},$$

and $$\frac{dM_z(t)}{dt} = \gamma \cdot (\vec{M}(t) \otimes \vec{B}(t))_z - \frac{M_z(t) - M_0}{T_1},$$

where $\gamma$ is the gyromagnetic ratio, $\otimes$ denotes a vector cross product and $\vec{B}(t)=(B_x(t), B_y(t), B_0+\Delta B_z(t))$ is the magnetic field experienced by a type of nuclei in the tissue sample. The parameters in the Bloch equations may include $T_1$, $T_2$, a density of a type of nuclei, diffusion, velocity/flow, temperature, and magnetic susceptibility. Note that there may be different parameters for different types of nuclei for each of the voxels. Moreover, note that the Bloch equations are a semi-classical, macroscopic approximation to the dynamic response of the magnetic moments of the type of nuclei in the tissue sample to a time-varying magnetic field. For example, there may be 67 M cells in a 1 mm³ voxel.

In principle, the solution space for the parameters in the Bloch equations for the tissue sample may be underdetermined, i.e., there may be significantly more parameters to be determined than there are observations with which to specify or constrain the parameters. Therefore, the characterization technique may leverage additional information to constrain or reduce the dimensionality of the problem. For example, aspect of the anatomy of the tissue sample may be determined using other imaging techniques, such as computed tomography, x-ray, ultrasound, etc. Moreover, tissue that does not look like (i.e., that has very different MR signals) than a targeted type of tissue (such as heart tissue) may be excluded from the MR model. Alternatively or additionally, tissue that deviates significantly from the expected MR signals based on previous scans (e.g., anomalies or changes) may become the focus of the MR model, such as by using a contour map (e.g., a cubic spline) to bound the regions (or specify a boundary of the regions) where there are significant differences. Alternatively or additionally, the error between measured MR signals and simulated MR signals may be represented using one or more level-set functions, and the boundaries of regions with errors exceeding a threshold value may be determined based on the intersection of a plane corresponding to the threshold value and the one or more level-set functions. In addition, by performing scans at different magnetic-field strengths $B_0$ (which may provide similar information to pseudorandom pulse sequences) using different pulse sequences and/or different MR techniques, the ratio of parameters to observations may be reduced, thereby simplifying the determination of the MR model.

For example, if the tissue sample included one voxel, there may be 4-10 MR model parameters (which specify an invariant MR signature) that need to be determined for a particular type of tissue. If the voxel includes M types of tissue, there may be 4M-10M MR model parameters (which specify M invariant MR signatures) that need to be determined for the particular type of tissue. As the number of voxels increases, this can appear to be a daunting problem.

However, because different types of nuclei have different Larmor frequencies, the spatial distribution of the types of nuclei and their local concentrations may be determined from the measured MR signals. Then, a predefined anatomical template for the tissue sample (or a human body), with associated initial parameters for an MR model, may be scaled to match the spatial distribution of the types of nuclei and their local concentrations.

Next, for a type of tissue (such as a particular organ), the MR model parameters may be iteratively refined as the size of the voxels is progressively decreased (and, thus, the number of voxels is increased). This analysis may be driven by the error between the measured MR signals and simulated MR signals using the MR model. Over time, the focus during the training will be on the residual regions with errors that are larger than a convergence criterion. For example, the parameters in the MR model may be trained based on measured MR signals at one magnetic-field strength and then the error may be determined based on the predictions of the the MR model at another magnetic-field strength. Furthermore, note that initially the MR model may assume that there is no contribution or interaction between different voxels. However, as the error and the voxel size is reduced, subsequently such contributions and/or interactions may be included when training the MR model.

In order to facilitate this fitting or computational approach, the characterization technique may determine 'surface signatures,' as opposed to 1D signatures. For example, using measurements at multiple magnetic-field strengths or in the presence of known magnetic-field disturbances (such as rotation), a set of MR trajectories may be determined as 'fingerprints' that can be used to determine the invariant MR signature(s). Note that each MR trajectory may be defined by a magnetic-field function rather than a fixed magnetic-field strength.

In an exemplary embodiment, a simulation that is used to determine the MR model may be vertex/voxel centric. Using a physical model (such as a Bloch-equation-based model) running at each vertex, the system may 'apply' pulse sequences or disturbance to the physical model of the tissue sample being scanned. For example, a message may be broadcast to the vertices that describe the disturbance in terms of physical laws. Each of the vertices may compute its predicted change in state and the resulting forces and energies, which are then relayed as messages to adjacent vertices about the forces and energies exported from that vertex. When all the vertices have generated a message, the message has been forwarded to the adjacent vertices and the state of the system has been updated, a time interval in the calculation may be complete. This approach can be generalized so that the message is forwarded to non-cyclical paths of length N (where N is an integer) radiating out from the vertex to improve the accuracy of the simulation.

Once the state has been updated, a computational technique can be run over the new computed state and then compared to the measured state. The error may be the difference between the predicted state and the measured state. As the computational technique is applied, the system may determine how to optimally assign the current state to each vertex in a way that reduces or minimizes the global error. Next, the system may choose a new set of perturbations for the system and may broadcasts these as a new message to the vertices, as well as executing this disturbance physically on the subject being scanned. In this way, the system may provide real-time or near-real-time analysis and feedback during the characterization technique.

Thus, the inverse problem of determining the MR model parameters based on measured MR signals may be 'solved' by minimizing the error or difference between the measured MR signals and simulated MR signals that are generated based on the MR model, characteristics of the MR scanner (such as magnetic-field inhomogeneity) and the scanning instructions used to acquire the measured MR signals. In some embodiments, the inverse problem is solved using one or more computational techniques, including: a least-squares technique, a convex quadratic minimization technique, a steepest descents technique, a quasi-Newton technique, a simplex technique, a Levenberg-Marquardt technique, simulated annealing, a genetic technique, a graph-based technique, another optimization technique and/or Kalman filtering (or linear quadratic estimation).

Note that the inverse problem may be solved using dynamic programming. In particular, the problem may be divided up and performed by multiple computers in parallel, e.g., in a cloud-based computing system. For example, a particular thread may attempt to solve the inverse problem for particular scanning instructions. Multiple potential parameter solutions generated by the computers (or processors) may be combined (e.g., using linear superposition) to determine an error metric that is minimized using the one or more computational techniques.

Moreover, as described previously, the inverse problem may be solved iteratively by first attempting to find suitable parameters (e.g., parameters that minimize the error between the MR signals and simulated MR signals) for the MR model using a coarse voxel size and then progressively finding suitable parameters with smaller voxel sizes. Note that the final voxel size used in this iterative procedure may be determined based on the gyromagnetic ratio of a type of nuclei being scanned. The voxel size can also be determined based on the kind of 'query' that is made to the biovault or that forms the based on the MR scan plan, the current hardware configuration and/or hardware limitations. Furthermore, the voxel size or locations may also be chosen so that a voxel is evenly portioned into a set of subvoxels, or so that there is certain amount of overlap with preview voxel sizes to effectively 'oversample; the overlapping region and potentially further localize where an MR signal originates. As described further below, this last technique may be akin to shifting the entire gradient system in one or more dimensions by a distance cbc that is less than a characteristic length of the voxels (such as a length, a width or a height of the voxels). In some embodiments, the voxel size in the MR model is smaller than that used in the MR scans (i.e., the MR model may use a super-resolution technique).

Additionally, the MR model may include simulations of dynamics, such as motion associated with: respiration, a heartbeat, blood flow, mechanical motion, etc. (Thus, there may be additional terms in the Bloch equations for diffusion, thermomemtry, spectroscopy, elastography, etc. Consequently, the MR model may be based on the Bloch-Torrey equations, etc.) For example, when a voxel contains a space that has a fluid flowing through it (such as in a vein), the flow of the liquid may be simulated by building a map of the flow directions and velocity magnitudes in the tissue sample (or subject) being scanned to be accounted for it the computation of the invariant MR signature. Furthermore, when scanning a human subject or an animal, the MR model may include the resting motion (such as that associated with respiration, a heartbeat, etc.). As noted previously, in order to facilitate calculation of the MR model, measured MR signals and/or other temporal measurements may be synchronized with or relative to a reference clock or a biological time period.

The MR model may be used to predict how the tissue sample will respond to particular scanning instructions. In particular, the MR model may be used to simulate or estimate the MR signals for a particular MR scanner having particular characteristics and for particular scanning instructions. Stated different, an invariant MR signature (which is based on the MR model) may be used to determine representations or projections (i.e., the MR signals) in particular contexts, such as based on the particular characteristics of the MR scanner and the particular scanning instructions.

Thus, the MR model may allow system 100 (FIG. 1) to perform active learning. In particular, the MR model may be iteratively fit or determined based on 'queries' generated by a learning system or a learning engine (which may be implemented in computer system 114 in FIG. 1). In particular, the queries generated by the learning engine may include different magnetic-field strengths $B_0$, different electromagnetic pulse sequences and/or different ultrasonic pulse sequences that are based on confidence intervals for parameters in the MR model. Consequently, the learning engine may use the measured MR signals in response to these queries to determine unknown parameters in the MR model and/or parameters having a poor accuracy (such as a confidence interval greater than 0.1 1, 5 or 10%). More generally, the adaptive learning performed by system 100 (FIG. 1) may be based on a wide variety of measurements, such as optical/infrared spectroscopy, x-ray, computed tomography, proton beam, photoacoustic, ultrasound, etc.

While the preceding discussion used the Bloch equations as an illustrative example, in other embodiments full Liouvillian computations (such as a Liouville supermatrix of interactions between two or more elements) or another simulation technique are used. Note that the MR signals computed or predicted using the MR model may be sampled at a rate equal to or higher than twice the Nyquist frequency of MR signals acquired during an MR scan.

In an exemplary embodiment, computer system 114 (FIG. 1) first approximates the parameters in the MR model and computes the error (or difference vector) between the measured MR signals and simulated MR signals based on this initial MR model. Note that when there are multiple candidate parameter solutions (having similar errors) to the inverse problem for a thread corresponding to particular scanning instructions, computer system 114 (FIG. 1) may keep the candidates (i.e., a unique parameter solution may not be identified at this point in the calculation). Alternatively, if there is no unique parameter solution within a desired error range (such as less than 50, 25, 10, 5 or 1%), the best (least-error) parameter solution may be kept. In addition, when there is no parameter solution within the desired error range, computer system 114 (FIG. 1) may modify the scanning instructions.

Moreover, computer system 114 (FIG. 1) may compute first and second derivatives along a surface(s) of parameter solutions in the tissue sample. (In order to facilitate calculation of a derivative, note that the parameters may be represented using one or more level-set functions.) A set of voxels along the line where the first derivative is zero may be identified. This set of voxels may be fit using a cubic spline with a minimum error between the voxel positions and the cubic spline. This fitting operation may be repeated at all the boundaries in the parameter-solution space. Moreover, the largest continuous surface within the boundary defined by the cubic splines may be determined and the parameter-solution calculation may be repeated to determine a new continuous surface that is within the previous continuous surface. This generalized framework may minimize the error across intra-voxel volumes, thereby improving the agreement between the MR signals and the simulated MR signals based on the MR model.

We now describe embodiments of how to determine a distribution of types of tissue. Using MRF as an illustration, define a dictionary $D_{mrf}$ of measured time sampled MR trajectories (or vectors) for different types of tisse dj (for j=1 to n) such that a measured MR signal $y_{obv}$ for a voxel can be expressed as $$y_{obv} = \sum_{j=1}^{n} \alpha_j \cdot d_j + \varepsilon,$$

where $\alpha_j$ are normalized weights (i.e., $$\left(i.e., \sum_{j=1}^{n} \alpha_j = 1\right)$$

and ε is an error (i.e., $\varepsilon=(y_j, \alpha_j)$, for j=1 to n. This may define an intra-voxel linear equation problem. A generalized inter-voxel problem may model a set of voxels (such as a cube with 27 voxels) as a graph G. As shown in FIG. 3, every voxel in the set may have 26 edges to eight adjacent voxels. A parameter solution to the inverse problem may be defined as one that minimizes the error.

Consider the case of two adjacent voxels u and v. The intra-voxel linear equations $U_y$ and $V_y$ need to be solved at both u and v. There are several possible outcomes. First, $U_y$ and $V_y$ may have unique parameter solutions (where a 'unique parameter solution' may be a best fit to an existing MR model, i.e., with an error or difference vector that is less than a convergence criterion) and the analysis may be finished. Alternatively, $U_y$ may have a unique parameter solution but not $V_y$. It may be possible that the parameter solution for $U_y$ imposes a constraint on $V_y$ such that $V_y$ has a single parameter solution, in which case the analysis may be finished. However, neither $U_y$ and $V_y$ may have unique parameter solutions, in which case combining the systems of equations (i.e., effectively increasing the voxel size) may yield a unique parameter solution. Moreover, neither $U_y$ and $V_y$ may have any parameter solutions, in which case the intra-voxel problem cannot be solved without further constraints.

In the last case, it may be possible to look at an adjacent voxel w, i.e., series voxels u, v and w, with the corresponding intra-voxel linear equations $U_y$, $V_y$ and $W_y$ need to be solved at u, v and w. Note that the intra-voxel linear equations $V_y$ and $W_y$ reduce to the previous case. When the intra-voxel linear equations do not reduce to the previous case, this paring operation can be applied recursively until it does and then the intra-voxel linear equations can be solved as described previously.

In general, this computational technique may be isomorphic to the problem of fitting a 3D surface (or volume) to minimize the error. One challenge in this regard is that it assumes that all adjacent volumes have an equal effect on the parameter solution $\alpha_j$ that minimizes the error.

The minimization of the error may initially assume that there is no inter-voxel contribution (i.e., that the voxels are independent). Subsequently, inter-voxel contributions may be included. In particular, considering adjacent voxel volumes, there are two distinct classes. Volumes that share a surface and volumes that only share a 1D edge. The minimization function can be improved by weighting the error contribution at voxel u at the center of the relative coordinate system. If the effect on the error is proportional to $r^{-2}$ (where r is the distance between center points of voxels) and assuming 1 mm isotropic voxels in the weightings, the minimization or fitting problem with inter-voxel contributions can be expressed as $$\min(\text{error}(y(0, 0, 0),$$
$$\alpha(0, 0, 0) + \frac{1}{(1)^2} \sum_{k=1}^{m} \text{error}(y_k, \alpha_k) + \frac{1}{(\sqrt{2})^2} \sum_{l=1}^{p} \text{error}(y_l, \alpha_l),$$

where the summation over k is for adjacent voxels sharing a common surface (i.e., (−1,0,0), (1,0,0), (0,−1,0), (0,1,0), (0,0,−1) and (0,0,1)) and the summation over l is for a remainder of adjacent voxels sharing a common edge. The assumption in the analysis is that the most difficult place to fit or determine parameter solutions is at discontinuities or interfaces between different tissues. Consequently, during the characterization technique, computer system 114 (FIG. 1) may solve these locations first and then may solve the remaining locations.

Alternatively, because the magnetic contribution from neighboring voxels is proportional to $r^2$, given a sphere of radius R from the center of a primary or central voxel in the minimization problem, surrounding voxels may be weighted based on the how much the sphere expands into the volume of the adjacent voxels (and, thus, based on how strong their inter-voxel contribution is estimated to be). For example, there may be three different weights that need to be assigned, including: a weight for voxels that share a 2D surface, a weight for voxels that share a 1D line, and a weight for voxels that share a 0D point. Because there may not be a uniform tissue distribution within each voxel, the weights may be dynamically adjusted to model different kinds of distributions inside each voxel in order find the distributions that minimize the error. This may provide the ability to identify multiple MR signatures within a single voxel for different types of tissue. Note that, as computational power increases, the accuracy of the predictive model may increase and the computational technique used to solve the minimization problem (and, thus, the inverse problem) may be modified.

Thus, in embodiments where the invariant MR signature of a voxel depends on the invariant MR signatures of surrounding or neighboring voxels, the invariant MR signature of a voxel may be computed using $2^{nd}$ or $N^{th}$-order effects. For example, if there are N $1^{st}$-order invariant MR signatures (where N is an integer), there may be as many as $N!/(N-27)!$ $2^{nd}$-order invariant MR signatures (if all the voxels interact with each other). In some embodiments, locality is used to simplifty the inverse problem. In this way, an invariant MR signature may be generated by incorporating how the invariant MR signatures in adjacent voxels effect the invariant MR signature in a primary (central) or $1^{st}$-order voxel.

In some embodiments, a dithering technique is used to overcome the arbitrary locations of the voxels relative to the distribution of types of tissue in the body. In particular, there may be two or more types of tissue in a voxel because of the arbitrary voxel placement or the current voxel size. This may significantly change the MR model parameters for this voxel. This may suggest that there is more than one invariant MR signature needed for the voxel. As described previously, in order to confirm this, the voxels may be displaced by a distance dx (which is a fraction of the voxel length, width or height) and the MR model parameters may be determined again. In the processes, the tissue distribution may be determined. Consequently, this approach may effectively increase the spatial resolution in the analysis without changing the voxel size.

Figure 4:
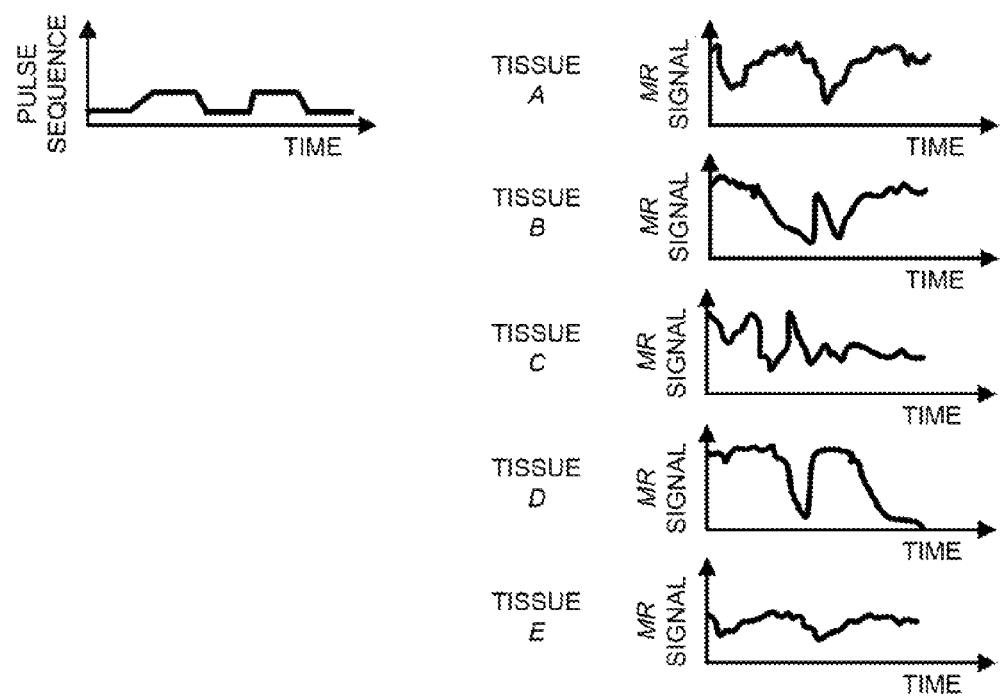
FIG. 4 is a drawing illustrating a set of MR signals as a function of time in accordance with an embodiment of the present disclosure.
Figure 5:
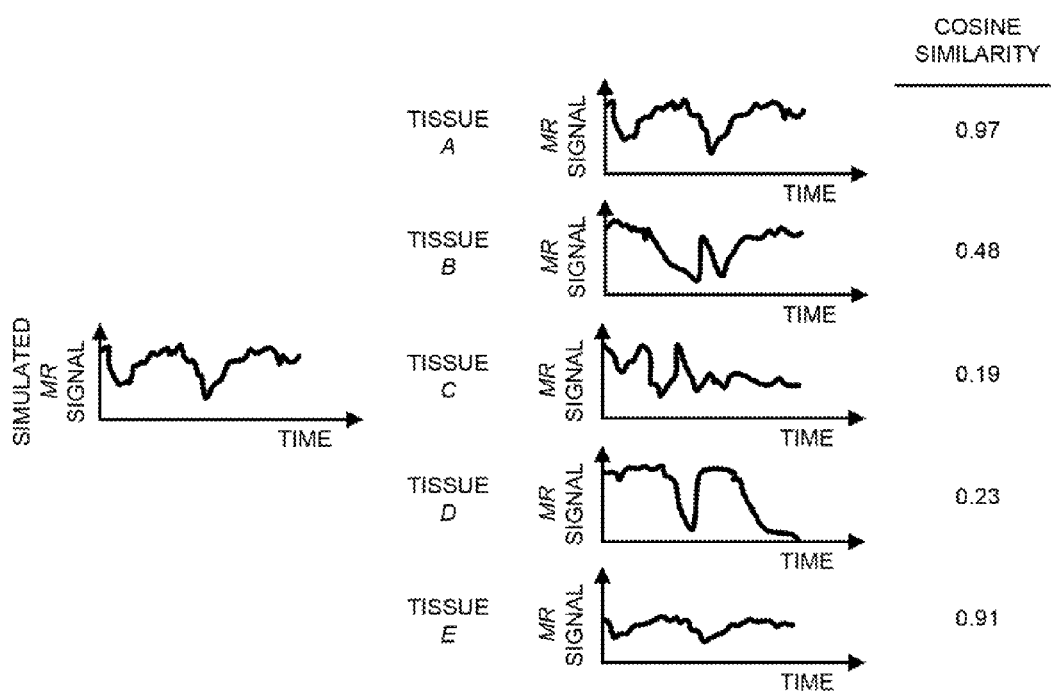

FIGS. 4-9 summarize the preceding discussion of determining parameters for one or more MR models that accurately predict MR signals and their use in the biovault. In particular, FIG. 4 presents a set of MR signals as a function of time that may be acquired during MR scans of different types of tissue using a particular pulse sequence and an applied magnetic field. Then, as shown in FIG. 5, for particular MR model parameters, a simulated MR signal as a function of time may be determined. The cosine similarity of this simulated MR signal may be computed with each of the measured MR signals for the different types of tissue.

Figure 6:
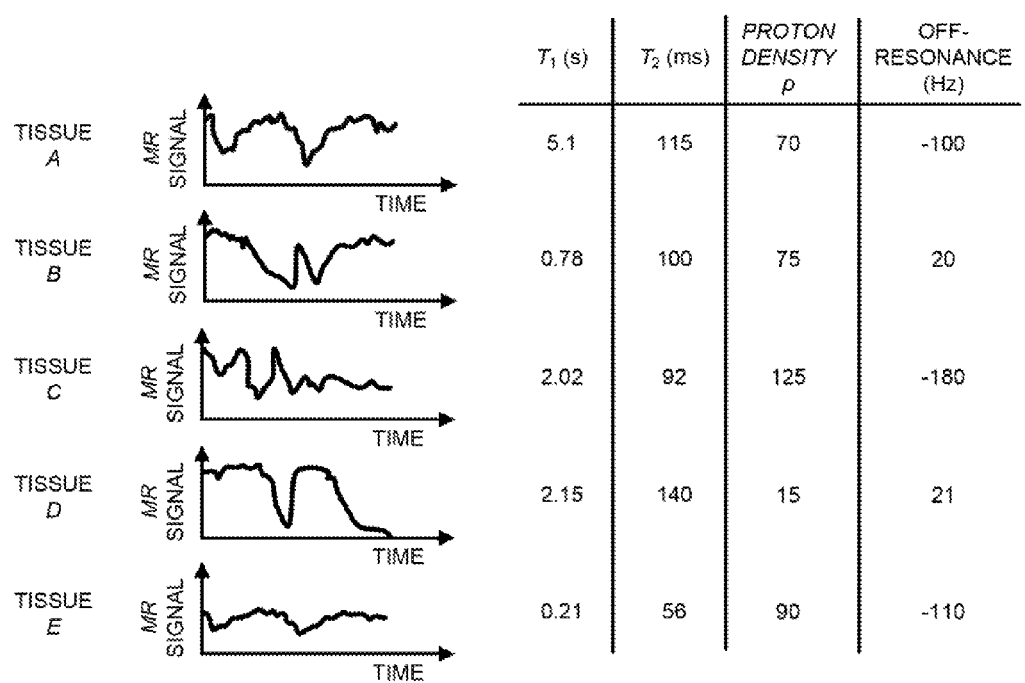
FIG. 6 is a drawing illustrating determined MR model parameters for the set of MR signals in FIG. 4 in accordance with an embodiment of the present disclosure.
Figure 7:
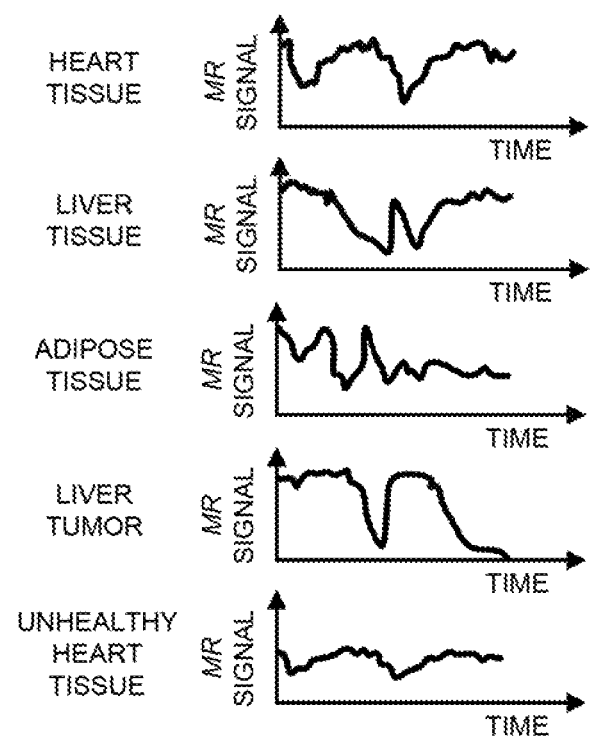
FIG. 7 is a drawing illustrating identifying different types of tissue in the set of MR signals in FIG. 4 in accordance with an embodiment of the present disclosure.
Figure 8:
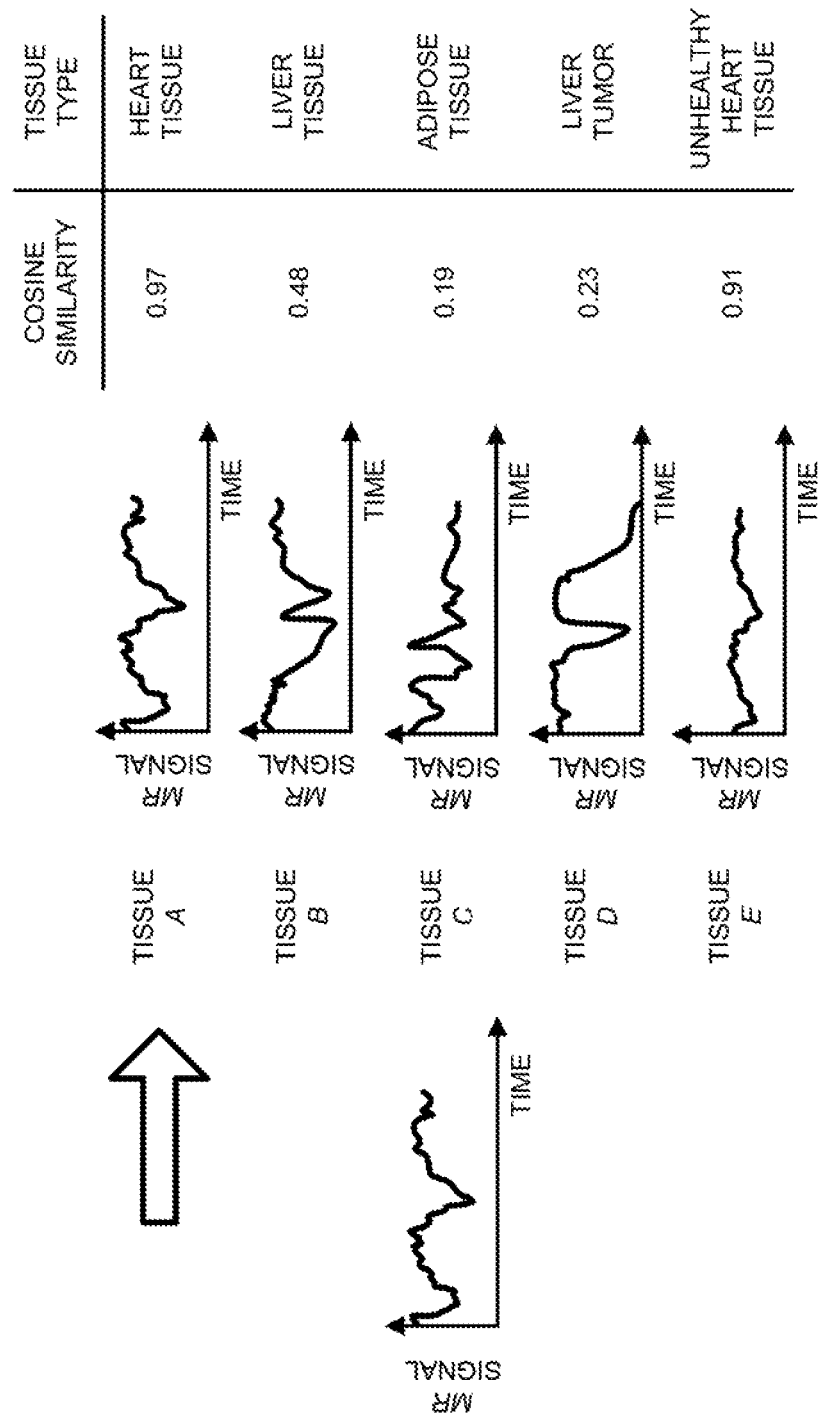
FIG. 8 is a drawing illustrating identifying MR signals as associated with a type of tissue in accordance with an embodiment of the present disclosure.

Moreover, FIG. 6 illustrates the determined MR model parameters for the different types of tissue. Next, as shown in FIG. 7, based on comparisons of the MR model parameters with known (or previously determined) MR model parameters for different types of tissue, the different types of tissue may be identified. For example, as shown in FIG. 8, based on the cosine similarity an MR signal may be identified as or associated with a particular type of tissue (in this example, healthy heart tissue).

Figure 9:
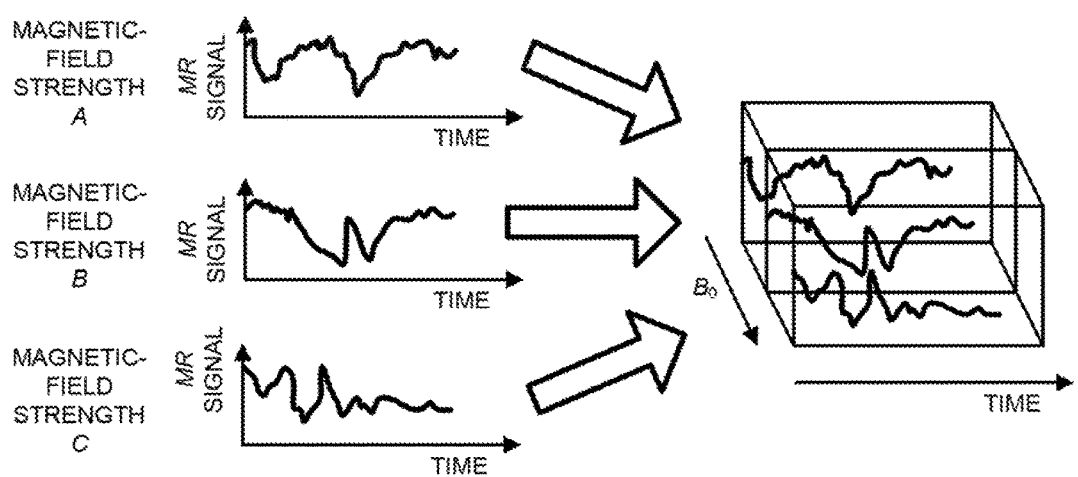
FIG. 9 is a drawing illustrating a set of MR signals that specify the response to a surface of magnetic-field strengths in accordance with an embodiment of the present disclosure.

Finally, as shown in FIG. 9, MR signals or trajectories acquired at different magnetic-field strengths may be combined into a set of MR signals that specify the response to a surface of magnetic-field strengths. This response may be used to determine one or more invariant MR signatures.

Figure 10:
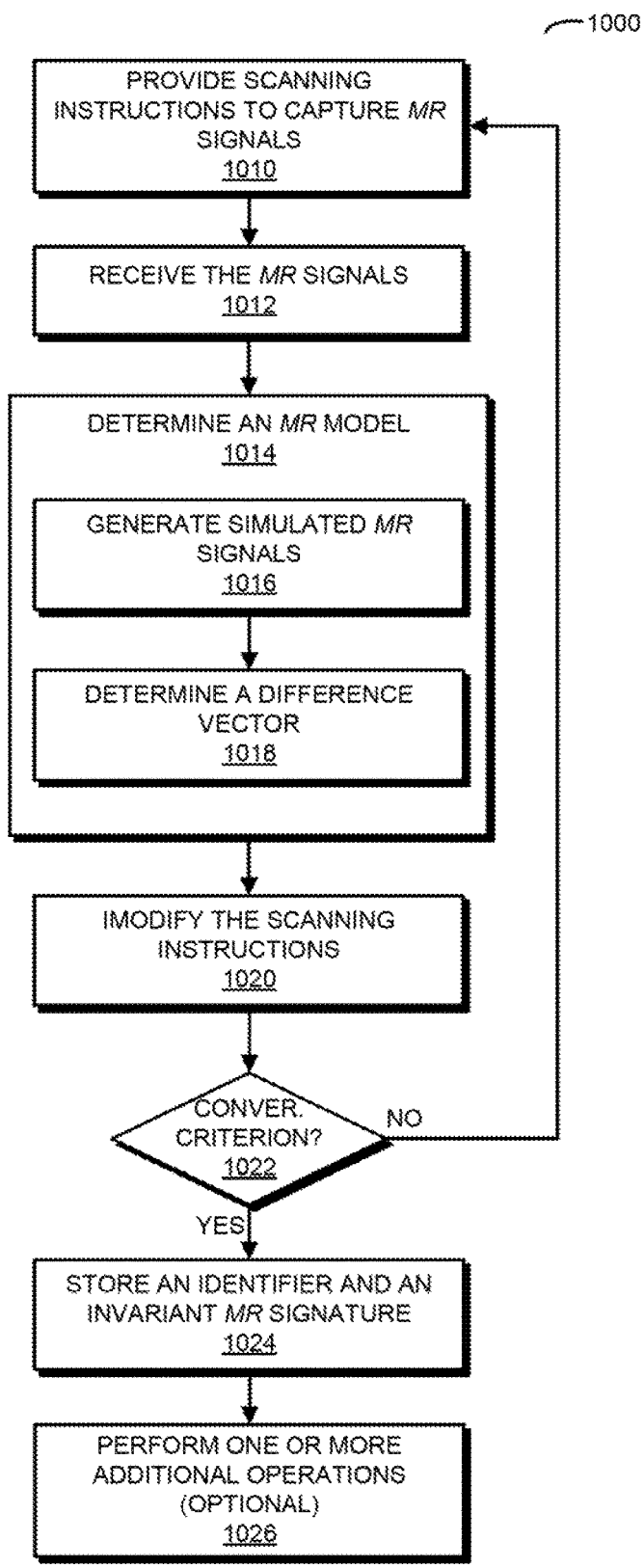
FIG. 10 is a flow diagram illustrating a method for determining an invariant MR signature in accordance with an embodiment of the present disclosure.

We now further describe the method. FIG. 10 presents a flow diagram illustrating an example of a method 1000 for determining an invariant MR signature of a biological sample, which may be performed by a system, such as system 100 (FIG. 1). During operation, the system may determine an MR model of voxels at 3D positions in the biological sample based on differences of MR signals associated with the voxels and simulated MR signals. In particular, the system may provide, to an MR scanner, scanning instructions to capture MR signals (operation 1010) of one or more types of nuclei in the biological sample, where the MR signals are associated with the voxels at the 3D positions in the biological sample, and the scanning instructions include a magnetic-field strength and a pulse sequence that are applied to the biological sample.

Then, the system receives, from the MR scanner, the MR signals (operation 1012). Moreover, the system determines an MR model of the voxels (operation 1014) in the biological sample based on the MR signals and the scanning instructions, where determining the MR model involves: generating simulated MR signals (operation 1016) for the biological sample based on the MR model and the scanning instructions, and comparing the simulated MR signals and the MR signals to determine a difference vector (operation 1018).

Next, the system iteratively modifies the scanning instructions (operation 1020) based on the difference vector and repeats the providing (operation 1010), the receiving (operation 1012) and the determining (operation 1014) until a convergence criterion is achieved (operation 1022), where the modified scanning instructions include changes to at least one of the magnetic-field strength and the pulse sequence.

Furthermore, the system stores, in memory, an identifier of the biological sample and the invariant MR signature (operation 1024) of the biological sample that is associated with the MR model and that describes a dynamic MR response of the biological sample at an arbitrary magnetic-field strength.

In some embodiments, the system optionally performs one or more additional operations (operation 1026). For example, the system may: compare the invariant MR signature to one or more predetermined invariant MR signatures; determine a classification of the biological sample based on the comparisons; and store, in the memory, the determined classification with the identifier and the invariant MR signature.

Figure 11:
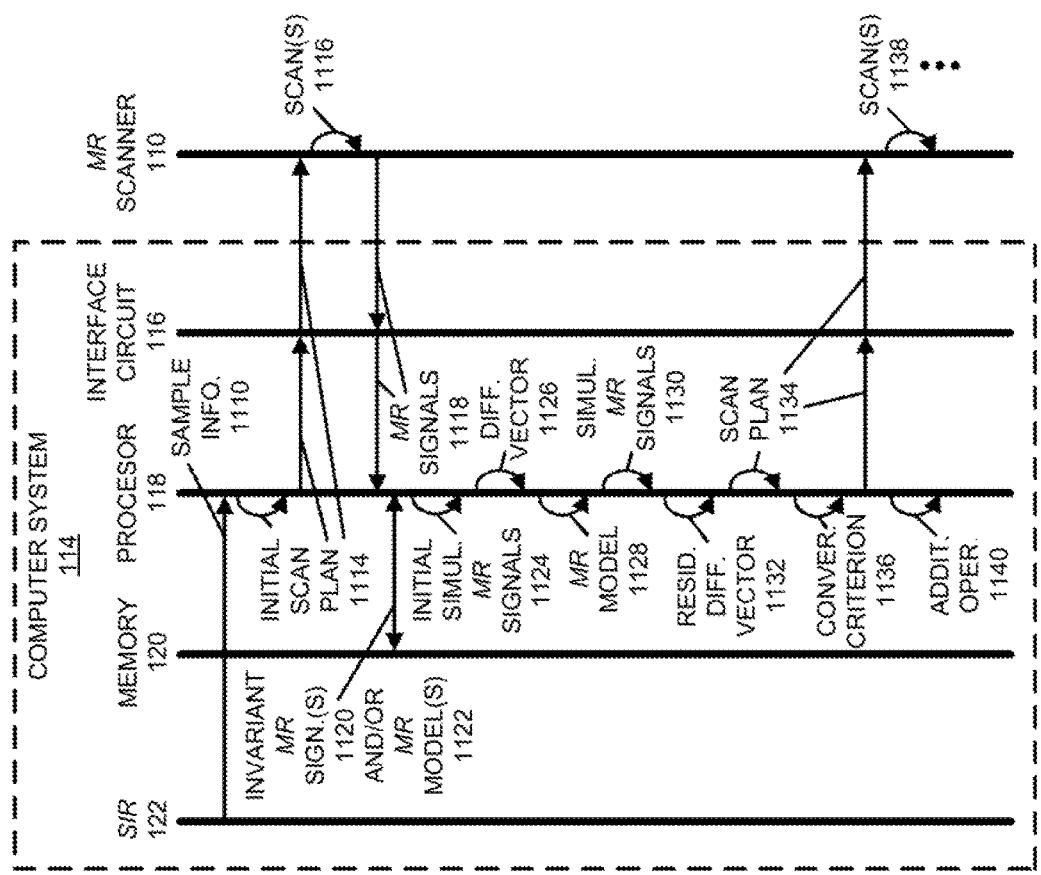
FIG. 11 is a drawing illustrating communication among components in the system in FIG. 1 in accordance with an embodiment of the present disclosure.

Embodiments of the classification technique are further illustrated in FIG. 11, which presents a drawing illustrating communication among components in system 100 (FIG. 1). In particular, processor 118 in computer system 114 may receive sample information 1110 from sample-information reader 122. In response, processor 118 may access predefined or predetermined information 1112 about tissue sample 112 (FIGS. 1 and 2) in memory 120 based on a unique identifier in sample information 1110. Based on this information, processor 118 may determine an initial scan plan 1114 (or scanning instructions), including: one or more MR techniques, one or more regions of interest in tissue sample 112 (FIGS. 1 and 2), one or more types of nuclei, one or more pulse sequences and/or one or more magnetic-field strengths.

Then, via interface circuit 116, processor 118 may instruct MR scanner 110 to perform one or more scans 1116 based on initial scan plan 1114. Next, MR scanner 110 provides MR signals 1118 to computer system 114. After receiving MR signals 1118, interface circuit 116 provides MR signals 1118 to processor 118. Processor 118 may compare MR signals 1118 to initial simulated MR signals 1124 to compute a difference vector 1126. For example, processor 118 may access one or more predetermined invariant MR signatures 1120 and/or one or more MR models 1122 in memory 120 based on the unique identifier, and processor 118 may generate the initial simulated MR signals 1124 based on initial scan plan 1114, characteristics of MR scanner 110, the one or more predetermined invariant MR signatures 1122 and/or the one or more MR models 1124.

Moreover, based on difference vector 1126, processor 118 may determine parameters in an MR model 1128 of voxels at 3D positions in tissue sample 112 (FIGS. 1 and 2). Furthermore, processor 118 may calculate a residual difference vector 1132 between MR signals 1118 and simulated MR signals 1130, which are generated using the resulting MR model 1128 and initial scan plan 1114. Based on residual difference vector 1132, processor 118 may modify initial scan plan 1114 to obtain scan plan 1134.

If a convergence criterion 1136 is not achieved, processor 118 may, via interface circuit 116, instruct MR scanner 110 to perform one or more scans 1138 based on scan plan 1134, and the operations in the characterization technique may repeat. Moreover, when convergence criterion 1136 is achieved, processor 118 may performs one or more additional operations 1140, such as determining a classification of tissue sample 112 (FIGS. 1 and 2) and/or determining an invariant MR signature for tissue sample 112 (FIGS. 1 and 2) based on a final version of the MR model. For example, the invariant MR signature may include parameters in the final version of the MR model and additional information that allows MR signals to be generated based on the invariant MR signature. Then, processor 118 may store information in memory 120, such as the unique identifier, the invariant MR signature, other measurement results and/or information (such as metadata) about tissue sample 112 (FIGS. 1 and 2).

In some embodiments of one or more of the preceding methods, there may be additional or fewer operations. Furthermore, the order of the operations may be changed, and/or two or more operations may be combined into a single operation.

Note that in some embodiments the characterization technique is used to dynamically scan, capture, and process MR signals for a tissue sample that are associated with one or more MR techniques. For example, the one or more MR techniques may be used to perform, in series or parallel, soft-tissue measurements, morphological studies, chemical-shift measurements, magnetization-transfer measurements, MRS, measurements of one or more types of nuclei, Overhauser measurements, and/or functional imaging. In addition, additional measurements may be performed on the tissue sample. Subsequently, the resulting invariant MR signatures, which may have high-spatial and spectral resolution, and may incorporate the information in MRF, may be aggregated or indexed and searched to facilitate a variety of medical information services. In the discussion that follows, indexing quantitative profiles of specific healthy (or asymptomatic or non-diseased) and diseased (or symptomatic) tissue samples is used as illustrative example.

In some embodiments, initial scan 1114 plan includes an MR scan using a low magnetic field or no magnetic field MR scan (e.g., RF only) or a measurement other than MR, such as synthetic aperture radar (SAR), to scan for ferromagnetic or paramagnetic materials (e.g., metal plates, pins, shrapnel, other metallic or foreign bodies) in tissue sample 112 (FIGS. 1 and 2) or a body (if the MR scan is to be performed in-vivo). Alternatively or additionally, the initial scan may use electron-spin resonance. The initial scan for paramagnetic materials can improve safety in the system when MR scanning is used. This may be useful in case a patient's medical record does not include information about foreign objects, the foreign objects are new or unknown (e.g., shrapnel fragments remaining in a wound or in excised tissue), or in the event of an error. In particular, this 'safety scan' can prevent damage to tissue sample 112 (FIGS. 1 and 2) or injury to the patient, and can protect the system from damage. In addition, the size of any ferromagnetic or paramagnetic material can be estimated during initial scan 1114, and a safe magnetic-field strength for use during the MR scan can be estimated. Conversely, if tissue sample 112 (FIGS. 1 and 2) or a patient does not contain any ferromagnetic of paramagnetic materials, one or more higher magnetic-field strengths can be used during one or more subsequent MR scans.

In general, most non-diseased tissue samples in hospitals are evaluated by a medical specialist (such as a pathologist) and then destroyed. However, government regulations and laws often require that certain pathology samples are stored for a specific amount of time before they can be destroyed. Currently, there are no large standardized datasets that contain routinely symptomatic and asymptomatic tissue samples for comparison and improvement of medical diagnoses and that allow researchers to compare new tissue samples against an archive of historical sample measurements.

The indexed tissue samples may be characterized and normalized quantitatively so that their digital representation can be uploaded to a service where analysis techniques can, in real-time or near real-time, compare the sample quantitatively to a vast data structure (such as the biovault, which is sometimes referred to as a 'pathology characteristics knowledge base') containing numerous previously indexed ex vivo and in vivo tissue samples (including fresh or 'wet' tissue samples, frozen samples, formalin fixed-paraffin embedded samples, etc.). This capability may require that the characterization technique be largely invariant to the type of sample being indexed, the MR scanner used, as well as the pulse sequences and the magnitude of the magnetic fields (or the magnetic-field strengths) used to index the tissue samples. For example, the data structure may include invariant MR signatures that can be used to generate MR fingerprints for arbitrary scanning conditions (such as an arbitrary magnetic field $B_0$ and an arbitrary pulse sequence), and the generated MR fingerprints may be compared to a measured MR fingerprint.

The creation of this data structure may aid in the detection of pathological tissue in vivo by allowing the differences between healthy and unhealthy tissue to be classified or to identify other anomalous tissue that has not been previously classified. This capability may help determine the parts of a tissue sample that may require more detailed scans of detected anomalies. For example, an analysis technique (such as a supervised-learning technique, e.g., a support vector machine, classification and regression trees, logistic regression, linear regression, nonlinear regression, a neural network, a Bayesian technique, etc.) may classify anomalies as healthy or unhealthy tissue based on previous measurements and classifications in the data structure and features in MR signals measured in a current scan. Alternatively or additionally, images may be provided to radiologists or pathologists who specialize in the type of tissue or the anomaly detected, and the radiologists or pathologists may confirm the analysis or may classify the tissue sample.

In this way, tissue samples from biopsies, whether benign or non-benign, can be indexed, and known-healthy (e.g., whitelisted tissue) and known-anomalous tissue (e.g., blacklisted tissue) can be determined, and unknown tissue in a grey zone (e.g., greylisted tissue) can be classified. The unknown tissue may be marked for inspection using other MR techniques, additional related biopsies, radiologist or pathologist review, and/or using another analysis technique.

Note that the invariant MR signatures may be used to improve detection of anomalies on an individual basis. In particular, what is normal in one individual may be slightly different than what is normal in another individual, and clusters of tissue samples reflecting various shades or gradations of 'normal' can help classify tissue. (Thus, in some embodiments, the characterization technique may include an unsupervised-learning technique, such as clustering, to group or classify similar tissue samples to facilitate classification.) Furthermore, note that the amount of data that can be captured about each tissue sample may be much larger than the amount of data that can be processed by a single pathologist or radiologist or even a team of radiologists and pathologists. The invariant MR signatures in the data structure may be used to compensate for or eliminate this limitation or constraint.

In some embodiments, the invariant MR signature from a previous scan of a tissue sample (or a related or similar tissue sample) is used as a target for comparison to the MR signals during a current scan of the tissue sample. For example, the previous invariant MR signature may be used to generate estimated MR signals from voxels in a tissue sample in the current scan based on the characteristics of an MR scanner and/or the scanning instructions. In particular, the previous invariant MR signature may include or may specify parameters in an MR model that can be used, in conjunction with the characteristics of an MR scanner and/or the scanning instructions, to generate the estimated MR signals. Subsequently, the estimated MR signals can be used as a target to compare with the MR signals in the current scan. This may allow rapid identification of areas or regions with unexpected changes, which may allow identification of the parts of the tissue sample that may require more detailed scans of detected anomalies and/or measurement of different parameters (i.e., which may allow a scan plan to be dynamically updated). This capability may allow more efficient (i.e., faster) and more accurate scans of the tissue sample, such as by allowing: different scanning instructions, different MR techniques, and/or different voxels sizes to be used in different portions or regions of the tissue sample (e.g., larger voxels sizes in less interesting regions and smaller voxel sizes in regions that require more detailed scans).

In some embodiments, the characterization technique uses so-called 'breadth-first indexing' as a form of compressed sensing. In particular, the system may spend more time scanning and modeling interesting or dynamic parts of a tissue sample, and may avoid spending time on parts that are not changing rapidly. Note that 'interesting' regions may be determined based on information gathered in real-time and/or based on historical information about the tissue sample being scanned. Such breadth-first indexing may employ inference or inductive techniques such as oversampling and/or changing the voxel size based on an estimated abundance of various chemical species or types of nuclei (which may be determined using chemical shifts or MRS).

Flow-velocity mapping/modeling followed by MRS to determine a kind of infarction illustrates such breadth-first or dynamic indexing. In particular, analysis of flow parameters in the MR model may allow an obstruction to be identified. The location of an infarction in a blood vessel (such as an artery or a vein) may be determined without directly measuring the flow based on changes in blood flow velocities or parameters in the MR model that indicate increased blood pressure or turbulence. Moreover, based on Bernoulli's law, the narrowing of a blood vessel can be inferred without directly imaging plaque or a thrombosis. Then, the accuracy of this determination can be increased by performing MRS in the identified region to to see if there has been an increase in the chemical signature expected from plaque buildup.)

Note that in order to use the previous invariant MR signature to generate the estimated MR signals, a registration technique may be used to align the tissue sample with reference markers at known spatial locations or with the voxels in the previous invariant MR signature. This registration technique may use a global or a local positioning system to determine changes in the position of the tissue sample relative to an MR scanner. Alternatively or additionally, the previous invariant MR signature may be used during virtual registration of the tissue sample. For example, the previous invariant MR signature may be used to generate estimated MR signals for sets of voxels. The estimated MR signals in a given set of voxels may be averaged, and the resulting average MR signals in the sets of voxels may be compared to MR signals measured during a current scan to determine a static (or a dynamic) offset vector. For example, the positions of the average MR signals in the set of voxels (such as average MR signals in 3, 6, 12 or 24 regions or portions of a tissue sample) may be correlated (in 2D or 3D) with the MR signals in the set of voxels in the current scan. This offset vector may be used to align the MR signals and the estimated MR signals during subsequent comparisons or analysis. In some embodiments, the registration or the offset vector of a tissue sample is computed based on variation in the Larmor frequency and the predetermined spatial inhomogeneity or variation in the magnetic field of an MR scanner.

In some embodiments, the registration technique involves detecting the edges in node/voxel configurations. Because of the variability of anatomy across different tissue samples and subjects, transforming small variations of data into more generalized coordinates may be used to enable analysis and to generalize the results to a population. In general, the transforms may be one-to-one and invertible, and may preserve properties useful for identification and diagnostics, such as: curves, surfaces, textures and/or other features. For example, the features may be constrained to diffeomorphic transformations (such as smooth invertible transformations having a smooth inverse) or deformation metric mappings computed via geodesic flows of diffeomorphisms. In some embodiments, a diffeomorphic transformation between surfaces is used to compute changes on multi-dimensional structures (e.g., as a function of time).

Furthermore, linear combinations of diffeomorphic transformations computed based on sets of matches between MR signals and simulated MR signals associated with one or more invariant MR signatures (or linear combinations of invariant MR signatures) can provide spatial offset corrections based on a piori estimated information (such as motion, deformation, variations in anatomy, magnetic field, environmental conditions, etc.). These spatial offset corrections may be used as a weighted component in a supervised-learning registration engine. For example, a set of diffeomorphic velocity fields tracking a set of points across a set of phases of distortion (caused by movement of the lungs during regular breathing, the heart during heartbeat motion or a muscle during contraction or expansion) can be applied to a region of the body corresponding to the sets of points in the region (e.g., a set of voxels in or around the heart or lungs).

Thus, the characterization technique may allow hospitals and research institutions to catalogue and index many or even all of their tissue samples in a searchable way, and may allow a large data structure of indexed symptomatic and asymptomatic tissue samples to be amassed in an efficient manner (i.e., the characterization technique may be scaled to a large number of tissue samples) to provide clinically relevant results.

For example, when a region of interest is identified in a tissue sample (manually by an operator or technician and/or automatically based on comparisons with estimated MR signals based on previous invariant MR signatures for this tissue sample), a search may be automatically performed against the stored invariant MR signatures for other tissue samples and/or clinical research that have similar region(s) based on tissue parameters in the region of interest. These searches may surface similar cases and outcomes, with known diagnoses, to a radiologist analyzing the measurements on the tissue sample.

In some embodiments, the data structure includes a set of statistical definitions of pathology based on research, clinical definitions, previous tissue-sample scans, and/or statistical associations or pathology risk scores with previous pathological cases. The pathology risk scores may be computed for a specific tissue sample from a specific subject for a specific pathology that includes, but is not limited to, the statistical probability that the subject has the specific pathology or is at risk for developing the specific pathology. Moreover, the pathology risk scores may be stored in a lookup table based on the invariant MR signatures. Alternatively, the pathology risk scores may be stored in a lookup table based on MR signals, MR spectra and/or MR fingerprints, which each may be representations or projections of the invariant MR signatures in particular contexts, such as for a particular MR scanner having particular characteristics and particular scanning instructions. Furthermore, the invariant MR signatures may be linked to specific pathologies and diseases, as determined from scans of known good and known bad tissue samples, negative and positive-result biopsies, higher-specificity scans performed around particular or anomalous regions, radiologist feedback, etc. The data structure may be manually updated by technicians, researchers, doctors, journals, and/or other sources. Alternatively or additionally, the data structure may be automatically updated with additional tissue-sample information, and/or using a crawler that analyzes scientific publications and automatically extracts or scrapes research results and translate them or integrates them into pathology risk scores.

Moreover, in some embodiments, the data structure includes one or more dimensional animations of a body or a portion of a body over time (e.g., over weeks, months or years, or during a surgery) based on multiple invariant MR signatures of a tissue sample that are acquired at different times.

While the preceding discussion illustrated the use of MR techniques in the characterization technique, this approach may be generalized to a measurement system that is able to physically model and measure a material in real-time using a wide variety of measurement techniques (including one or more of the other measurements performed on the tissue sample). In general, this measurement system can use a combination of mechanical and/or electromagnetic waves to 'perturb' the volume being scanned in order to evaluate the correctness of a prediction in terms of how the volume will respond to these perturbations. This also includes the ability for the measurement system to simulate itself and any part of the environment in which the measurement system is located that could affect the correctness of the predictive model the measurement system is trying to generate to describe the volume being scanned.

Figure 12:
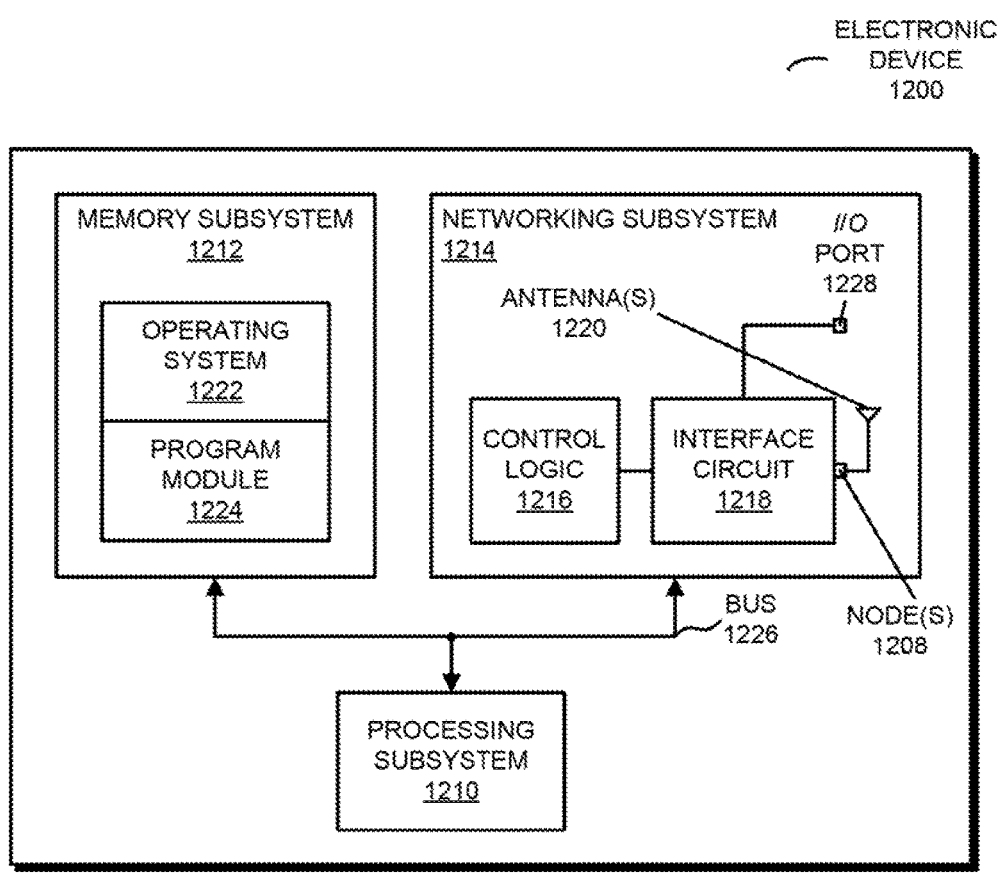
FIG. 12 is a block diagram illustrating an electronic device in the system of FIG. 1 in accordance with an embodiment of the present disclosure.

The result of this characterization may be a (4+N)D (three spatial dimensions, one time dimension, and N measurement dimensions at each point in space) quantitative model of the volume being scanned. In embodiments where the material being scanned is biological tissue, the measurement system is sometimes referred to as a 'bioinformatic measurement system' or a 'bioinformatic scanner.' Thus, the characterization technique may involve MR techniques other than MRI or may include MRI. Note that the (4+N)D quantitative model may be projected onto an arbitrary subset of the full (4+N)D space, including 2D or 3D images We now further describe an electronic device that performs at least some of the operations in characterization technique. FIG. 12 presents a block diagram illustrating an example of an electronic device 1200 in system 100 (FIG. 1), such as computer system 114 (FIG. 1) or another of the computer-controlled components in system 100 (FIG. 1). This electronic device includes a processing subsystem 1210, memory subsystem 1212, and networking subsystem 1214. Processing subsystem 1210 may include one or more devices configured to perform computational operations and to control components in system 100 (FIG. 1). For example, processing subsystem 1210 may include one or more microprocessors, application-specific integrated circuits (ASICs), microcontrollers, programmable-logic devices, and/or one or more digital signal processors (DSPs).

Memory subsystem 1212 may include one or more devices for storing data and/or instructions for processing subsystem 1210 and networking subsystem 1214. For example, memory subsystem 1212 may include dynamic random access memory (DRAM), static random access memory (SRAM), and/or other types of memory. In some embodiments, instructions for processing subsystem 1210 in memory subsystem 1212 include one or more program modules 1224 or sets of instructions, which may be executed in an operating environment (such as operating system 1222) by processing subsystem 1210. Note that the one or more computer programs may constitute a computer-program mechanism or a program module (i.e., software). Moreover, instructions in the various modules in memory subsystem 1212 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 1210.

In addition, memory subsystem 1212 may include mechanisms for controlling access to the memory. In some embodiments, memory subsystem 1212 includes a memory hierarchy that comprises one or more caches coupled to a memory in electronic device 1200. In some of these embodiments, one or more of the caches is located in processing subsystem 1210.

In some embodiments, memory subsystem 1212 is coupled to one or more high-capacity mass-storage devices (not shown). For example, memory subsystem 1212 may be coupled to a magnetic or optical drive, a solid-state drive, or another type of mass-storage device. In these embodiments, memory subsystem 1212 may be used by electronic device 1200 as fast-access storage for often-used data, while the mass-storage device is used to store less frequently used data.

In some embodiments, memory subsystem 1212 includes a remotely located archive device. This archive device can be a high-capacity network attached mass-storage device, such as: network attached storage (NAS), an external hard drive, a storage server, a cluster of servers, a cloud-storage provider, a cloud-computing provider, a magnetic-tape backup system, a medical records archive service, and/or another type of archive device. Moreover, processing subsystem 1210 may interact with the archive device via an application programming interface to store and/or access information from the archive device.

An example of the data stored (locally and/or remotely) in memory subsystem 1212 is shown in FIG. 13, which presents a drawing illustrating an example of a data structure 1300 that is used by electronic device 1200 (FIG. 12). This data structure may include: an identifier 1310-1 of tissue sample 1308-1, label information 1312 (such as the subject age, gender, an organ tissue sample 1308-1 was sampled from, the procedure during which tissue sample 1308-1 was taken, the time and place the sample was removed, the type of sample, the biopsy results and diagnosis if one has already been made and/or any other suitable sample information), timestamps 1314 when data was acquired, received MR signals 1316 (and, more generally, raw data), MR capture and model parameters 1318 (including the voxel size, speed, resonant frequency, $T_1$ and $T_2$ relaxation times, signal processing techniques, RF pulse techniques, magnetic gradient strengths, the variable magnetic field $B_0$, the pulse sequence, etc.), metadata 1320 (such as information characterizing tissue sample 1308-1, demographic information, family history, etc.), environmental conditions 1322 (such as the temperature, humidity and/or pressure in the room or the chamber in which tissue sample 1308-1 was measured), a determined invariant MR signature 1324, one or more additional measurements 1326 of physical properties of tissue sample 1308-1 (such as sample properties, e.g., weight, sample dimensions, images, etc.), and/or transformed data 1328 generated from or in response to MR signals 1316 (such as an estimated invariant MR signature). Note that data structure 1300 may include multiple entries for different scanning instructions.

In one embodiment, data in data structure 1300 is encrypted using a block-chain or a similar cryptographic hash technique to detect unauthorized modification or corruption of records. Moreover, the data can be anonymized prior to storage so that the identity of a subject is anonymous unless the subject gives permission or authorization to access or release the subject's identity.

Referring back to FIG. 12, networking subsystem 1214 may include one or more devices configured to couple to and communicate on a wired, optical and/or wireless network (i.e., to perform network operations and, more generally, communication), including: control logic 1216, an interface circuit 1218, one or more antennas 1220 and/or input/output (I/O) port 1228. (While FIG. 12 includes one or more antennas 1220, in some embodiments electronic device 1200 includes one or more nodes 1208, e.g., a pad, which can be coupled to one or more antennas 1220. Thus, electronic device 1200 may or may not include one or more antennas 1220.) For example, networking subsystem 1214 can include a Bluetooth networking system (which can include Bluetooth Low Energy, BLE or Bluetooth LE), a cellular networking system (e.g., a 3G/4G network such as UMTS, LTE, etc.), a universal serial bus (USB) networking system, a networking system based on the standards described in IEEE 802.11 (e.g., a Wi-Fi networking system), an Ethernet networking system, and/or another networking system.

Moreover, networking subsystem 1214 may include processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for network subsystem 1214. Moreover, in some embodiments a 'network' between components in system 100 (FIG. 1) does not yet exist. Therefore, electronic device 1200 may use the mechanisms in networking subsystem 1214 for performing simple wireless communication between the components, e.g., transmitting advertising or beacon frames and/or scanning for advertising frames transmitted by other components.

Within electronic device 1200, processing subsystem 1210, memory subsystem 1212, networking subsystem 1214 may be coupled using one or more interconnects, such as bus 1226. These interconnects may include an electrical, optical, and/or electro-optical connection that the subsystems can use to communicate commands and data among one another. Although only one bus 1226 is shown for clarity, different embodiments can include a different number or configuration of electrical, optical, and/or electro-optical connections among the subsystems.

Electronic device 1200 may be (or can be) included in a wide variety of electronic devices. For example, electronic device 1200 may be included in: a tablet computer, a smartphone, a portable computing device, test equipment, a digital signal processor, a cluster of computing devices, a laptop computer, a desktop computer, a server, a subnotebook/netbook and/or another computing device.

Although specific components are used to describe electronic device 1200, in alternative embodiments, different components and/or subsystems may be present in electronic device 1200. For example, electronic device 1200 may include one or more additional processing subsystems, memory subsystems, and/or networking subsystems. Additionally, one or more of the subsystems may not be present in electronic device 1200. Moreover, in some embodiments, electronic device 1200 may include one or more additional subsystems that are not shown in FIG. 12.

Although separate subsystems are shown in FIG. 12, in some embodiments, some or all of a given subsystem or component can be integrated into one or more of the other subsystems or components in electronic device 1200. For example, in some embodiments the one or more program modules 1224 are included in operating system 1222. In some embodiments, a component in a given subsystem is included in a different subsystem. Furthermore, in some embodiments electronic device 1200 is located at a single geographic location or is distributed over multiple different geographic locations.

Moreover, the circuits and components in electronic device 1200 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 1214 (such as a radio) and, more generally, some or all of the functionality of electronic device 1200. Moreover, the integrated circuit may include hardware and/or software mechanisms that are used for transmitting wireless signals from electronic device 1200 and receiving signals at electronic device 1200 from other components in system 100 (FIG. 1) and/or from electronic devices outside of system 100 (FIG. 1). Aside from the mechanisms herein described, radios are generally known in the art and hence are not described in detail. In general, networking subsystem 1214 and/or the integrated circuit can include any number of radios. Note that the radios in multiple-radio embodiments function in a similar way to the radios described in single-radio embodiments.

While some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both.

In addition, in some of the preceding embodiments there are fewer components, more components, a position of a component is changed and/or two or more components are combined.

In the preceding description, we refer to 'some embodiments.' Note that 'some embodiments' describes a subset of all of the possible embodiments, but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A system to determine an invariant magnetic-resonance (MR) signature of a biological sample, comprising:
    an MR scanner configured to perform MR scans of the biological sample;
    an interface circuit, electrically coupled to the MR scanner, configured to communicate information with the MR scanner;
    a processor electrically coupled to the MR scanner; and
    memory, electrically coupled to the processor, storing a program module, wherein, when executed by the processor, the program module causes the system to perform the MR scans of the biological sample by performing one or more operations comprising:
        providing, to the MR scanner, scanning instructions to capture MR signals of one or more types of nuclei in the biological sample, wherein the MR signals are associated with voxels at three-dimensional (3D) positions in the biological sample, and wherein the scanning instructions include at least a magnetic-field strength and a pulse sequence to be applied to the biological sample; and
        receiving, from the MR scanner, the MR signals;
        determining an MR model of the voxels in the biological sample based on the MR signals and the scanning instructions, wherein the MR model is based at least in part on model parameters, a simulation technique and predetermined characteristics of the MR scanner, including magnetic-field inhomogeneity and noise characteristics, and wherein determining the MR model involves:
            generating simulated MR signals for the biological sample based on the MR model and the scanning instructions and
            comparing the simulated MR signals and the MR signals to determine a difference vector;
        iteratively modifying the scanning instructions based on the difference vector and repeating the providing, the receiving and the determining until a convergence criterion is achieved, wherein the modified scanning instructions include changes to at least one of the magnetic-field strength and the pulse sequence; and
        storing, in the memory, an identifier of the biological sample and an invariant MR signature of the biological sample that corresponds to the MR model after the convergence criterion is achieved and that describes a dynamic MR response of the voxels in the biological sample at an arbitrary magnetic-field strength and with predetermined characteristics of an arbitrary MR scanner.

2. The system of claim 1, wherein the identifier uniquely identifies the biological sample.

3. The system of claim 1, wherein the one or more operations comprise generating the identifier.

4. The system of claim 1, wherein the system further comprises a sample-information reader electrically coupled to the interface circuit; and
    wherein the one or more operations comprise receiving, from the sample-information reader, information that specifies the identifier.

5. The system of claim 1, wherein the system further comprises a measurement device, electrically coupled to the interface circuit, configured to measure a physical property of the biological sample;
    wherein the one or more operations comprise:
        receiving, from the measurement device, physical property information that specifies the measured physical property; and
        storing, in the memory, the physical property information with the identifier and the invariant MR signature.

6. The system of claim 5, wherein the physical property includes one of: a weight of the biological sample; one or more dimensions of the biological sample; an impedance of the biological sample; and an image of the biological sample.

7. The system of claim 6, wherein the measurement device includes one of: an imaging sensor; a scale; an impedance analyzer; a laser imaging system; and a microscope.

8. The system of claim 1, wherein the MR scanner includes a bore-type MR scanner having a bore diameter between 1 and 10 cm.

9. The system of claim 1, wherein the MR scanner includes a bore-type MR scanner that is enclosed in a chamber, defined by a surface, filled with an inert gas.

10. The system of claim 1, wherein the MR scanner includes a bore-type MR scanner that is enclosed in a chamber, defined by a surface, which is configured to have a pressure less than atmospheric pressure.

11. The system of claim 1, wherein the biological sample is enclosed in a vessel that is filled with an inert gas.

12. The system of claim 1, wherein the biological sample is enclosed in a vessel that has a pressure less than atmospheric pressure.

13. The system of claim 1, wherein the one or more operations comprise encrypting the invariant MR signature prior to storage in the memory.

14. The system of claim 1, wherein the biological sample is formalin fixed-paraffin embedded; and
    wherein the one or more operations comprise transforming the invariant MR signature into an estimated invariant MR signature of an in-vivo sample based on the MR model.

15. The system of claim 1, wherein the biological sample comprises an in-vivo sample.

16. The system of claim 1, wherein the one or more operations comprise:
    comparing the invariant MR signature to one or more predetermined invariant MR signatures;
    determining a classification of the biological sample based on the comparisons; and
    storing, in the memory, the determined classification with the identifier and the invariant MR signature.

17. The system of claim 1, wherein the one or more operations comprise:
    performing an additional MR measurement on the biological sample; and
    storing, in the memory, a result of the additional MR measurement with the identifier and the invariant MR signature.

18. The system of claim 14, wherein the additional MR measurement comprises one of: MR thermometry (MRT), MR spectroscopy (MRS), MR imaging, (MRI), magnetic-field relaxometry, and MR elastography (MRE).

19. A non-transitory computer-readable storage medium for use in conjunction with a magnetic-resonance (MR) scanner, the computer-readable storage medium storing a program module, wherein, when executed by the MR scanner, the program module causes the MR scanner to determine an MR signature of a biological sample by performing one or more operations comprising:
    providing, to the MR scanner, scanning instructions to capture MR signals of one or more types of nuclei in the biological sample, wherein the MR signals are associated with voxels at three-dimensional (3D) positions in the biological sample, and wherein the scanning instructions include at least a magnetic-field strength and a pulse sequence to be applied to the biological sample; and
    receiving, from the MR scanner, the MR signals;
    determining an MR model of the voxels in the biological sample based on the MR signals and the scanning instructions, wherein the MR model is based at least in part on model parameters, a simulation technique and predetermined characteristics of the MR scanner, including magnetic-field inhomogeneity and noise characteristics, and wherein determining the MR model involves:
        generating simulated MR signals for the biological sample based on the MR model and the scanning instructions and
        comparing the simulated MR signals and the MR signals to determine a difference vector;
    iteratively modifying the scanning instructions based on the difference vector and repeating the providing, the receiving and the determining until a convergence criterion is achieved, wherein the modified scanning instructions include changes to at least one of the magnetic-field strength and the pulse sequence; and
    storing, in the memory, an identifier of the biological sample and an invariant MR signature of the biological sample that corresponds to the MR model after the convergence criterion is achieved and that describes a dynamic MR response of the voxels in the biological sample at an arbitrary magnetic-field strength and with predetermined characteristics of an arbitrary MR scanner.

20. A method for determining a magnetic-resonance (MR) signature of a biological sample using an MR scanner, the method comprising:
    by a computer:
    providing, to the MR scanner, scanning instructions to capture MR signals of one or more types of nuclei in the biological sample, wherein the MR signals are associated with voxels at three-dimensional (3D) positions in the biological sample, and wherein the scanning instructions include at least a magnetic-field strength and a pulse sequence to be applied to the biological sample; and
    receiving, from the MR scanner, the MR signals;
    determining an MR model of the voxels in the biological sample based on the MR signals and the scanning instructions, wherein the MR model is based at least in part on model parameters, a simulation technique and predetermined characteristics of the MR scanner, including magnetic-field inhomogeneity and noise characteristics, and wherein determining the MR model involves:
        generating simulated MR signals for the biological sample based on the MR model and the scanning instructions and
        comparing the simulated MR signals and the MR signals to determine a difference vector;
    iteratively modifying the scanning instructions based on the difference vector and repeating the providing, the receiving and the determining until a convergence criterion is achieved, wherein the modified scanning instructions include changes to at least one of the magnetic-field strength and the pulse sequence; and
    storing, in the memory, an identifier of the biological sample and an invariant MR signature of the biological sample that corresponds to the MR model after the convergence criterion is achieved and that describes a dynamic MR response of the voxels in the biological sample at an arbitrary magnetic-field strength and with predetermined characteristics of an arbitrary MR scanner.

\* \* \* \* \*